(12) United States Patent
Zhong et al.

(10) Patent No.: US 9,744,203 B2
(45) Date of Patent: Aug. 29, 2017

(54) APPLICATION OF COMPOSITION IN PREPARING HEALTH CARE PRODUCT OR MEDICINE FOR PREVENTING AND TREATING LEUKOPENIA CAUSED BY RADIOTHERAPY AND CHEMOTHERAPY

(71) Applicant: JIANGZHONG PHARMACEUTICAL CO., LTD., Nanchang, Jiangxi (CN)

(72) Inventors: Hongguang Zhong, Nanchang (CN); Minzhi Yi, Nanchang (CN); Jianzhong Lu, Nanchang (CN)

(73) Assignee: JIANGZHONG PHARMACEUTICAL CO., LTD., Nanchang, Jiangxi (CN)

( * ) Notice: Subject to any disclaimer, the term of this patent is extended or adjusted under 35 U.S.C. 154(b) by 167 days.

(21) Appl. No.: 14/403,978

(22) PCT Filed: May 27, 2013

(86) PCT No.: PCT/CN2013/000623
§ 371 (c)(1),
(2) Date: Nov. 25, 2014

(87) PCT Pub. No.: WO2013/177948
PCT Pub. Date: Dec. 5, 2013

(65) Prior Publication Data
US 2015/0290275 A1 Oct. 15, 2015

(30) Foreign Application Priority Data
May 29, 2012 (CN) .......................... 2012 1 0169752

(51) Int. Cl.
| | |
|---|---|
| *A61K 36/00* | (2006.01) |
| *A61K 36/738* | (2006.01) |
| *A61K 36/068* | (2006.01) |
| *A61K 36/074* | (2006.01) |
| *A61K 36/258* | (2006.01) |
| *A61K 36/344* | (2006.01) |
| *A61K 36/36* | (2006.01) |
| *A61K 36/481* | (2006.01) |
| *A61K 36/73* | (2006.01) |
| *A61K 36/062* | (2006.01) |
| *A61K 9/00* | (2006.01) |
| *A61K 9/20* | (2006.01) |
| *A61K 9/08* | (2006.01) |
| *A61K 9/14* | (2006.01) |
| *A61K 9/16* | (2006.01) |
| *A61K 9/48* | (2006.01) |

(52) U.S. Cl.
CPC .......... *A61K 36/738* (2013.01); *A61K 36/062* (2013.01); *A61K 36/068* (2013.01); *A61K 36/074* (2013.01); *A61K 36/258* (2013.01); *A61K 36/344* (2013.01); *A61K 36/36* (2013.01); *A61K 36/481* (2013.01); *A61K 36/73* (2013.01); *A61K 9/0056* (2013.01); *A61K 9/0095* (2013.01); *A61K 9/08* (2013.01); *A61K 9/141* (2013.01); *A61K 9/1605* (2013.01); *A61K 9/2004* (2013.01); *A61K 9/4841* (2013.01)

(58) Field of Classification Search
None
See application file for complete search history.

(56) References Cited

U.S. PATENT DOCUMENTS

2009/0004302 A1    1/2009    Cyr

FOREIGN PATENT DOCUMENTS

| CN | 1429954 | | 7/2003 |
|---|---|---|---|
| CN | 1883640 | | 12/2006 |
| CN | 1931336 A | * | 3/2007 |
| CN | 1970036 A | * | 5/2007 |
| CN | 1970036 A | | 5/2007 |
| CN | 101292742 A | | 10/2008 |
| CN | 100469384 C | | 3/2009 |
| CN | 101611870 | | 12/2009 |
| CN | 101623338 A | | 1/2010 |
| CN | 101647567 A | * | 2/2010 |
| CN | 102000129 A | | 4/2011 |
| CN | 102125649 | | 7/2011 |
| CN | 102228252 A | | 11/2011 |
| CN | 102247487 A | * | 11/2011 |
| CN | 102274258 A | | 12/2011 |
| CN | 102274259 A | | 12/2011 |
| CN | 102406163 | | 4/2012 |

(Continued)

OTHER PUBLICATIONS

Wikipedia, accessed on Aug. 6, 2015, pp. 1-3.*
Shoenfeld et al, Benign familial leukopenia and neutropenia in different ethnic groups. European journal of haematology, (Sep. 1988) vol. 41, No. 3, pp. 273-277.*
Correa-Rocha et al, Preterm neonates show marked leukopenia and lymphopenia that are associated with increased regulatory T-cell values and diminished IL-7. Pediatric Research (2012), 71(5), 590-597.*
Aslan, Leukopenia in familial Mediterranean fever: case series and literature review with special emphasis on pathogenesis. Pediatric hematology and oncology, (Mar. 2014) vol. 31, No. 2, pp. 120-128.*

(Continued)

*Primary Examiner* — Qiuwen Mi
(74) *Attorney, Agent, or Firm* — Loza & Loza, LLP; Michael F. Fedrick

(57) ABSTRACT

The present invention relates to use of a composition in the manufacture of a health care product or medicament for preventing and treating leucopenia induced by radiotherapy or chemotherapy. The composition is made from raw materials comprising 5 to 200 parts by weight of *Ganoderma*, 5 to 150 parts by weight of Radix Panacis Quinquefolii or Radix Et Rhizoma Ginseng, 1 to 90 parts by weight of fermented *Cordyceps sinensis* powder and/or 1 to 120 parts by weight of Cordyceps, or is a composition consisting of water and/or alcohol extracts of the above raw materials as active components.

18 Claims, No Drawings

(56) References Cited

FOREIGN PATENT DOCUMENTS

| CN | 102247487 A | 7/2012 |
|---|---|---|
| DE | 20 2008 011721 | 12/2008 |

OTHER PUBLICATIONS

Berman et al, Leukopenia associated with repeated exchange transfusion in the newborn. American Journal of Pediatric Hematology/Oncology, (1980) vol. 2, No. 1, pp. 77-80.*

Webester et al, Evaluation of cyren-B as a leukocyte protecting agent in patients undergoing radiotherapy or chemotherapy for malignant lymphoma. Acta Radiol, (1961) vol. 56, No. 3, pp. 231-236.*

Liu, Cordyceps sinensis health supplement enhances recovery from taxol-induced leukopenia. Experimental biology and medicine (Maywood, N.J.), (Apr. 2008) vol. 233, No. 4, pp. 447-455.*

Kaneko et al, Accelerated recovery from cyclophosphamide-induced leukopenia in mice administered a Japanese ethical herbal drug, Hochu-ekki-to. Immunopharmacology (1999), vol. 44, No. 3, pp. 223-231.*

International Written Opinion with English translation for International Patent Application No. PCT/CN13/00623, dated Aug. 29, 2013; 13 pages.

Extended European Search Report issued on Nov. 18, 2015 for counterpart European Patent Application No. 13796295.7.

Database WPI, Week 200363, Thomson Scientific, London, GB, AN 2003-664629, XP002744929, Jul. 16, 2003.

Database WPI, Week 201167, Thomson Scientific, London, GB, AN 2011-K35736, XP002744935, Jul. 20, 2011.

Database WPI, Week 201246, Thomson Scientific, London, GB, AN 2012-E61375, XP002749947, Apr. 11, 2012.

Database WPI, Week 201006, Thomson Scientific, London, GB, AN 2010-A47275, XP002749948, Dec. 30, 2009.

Database WPI, Week 200737, Thomson Scientific. London. GB, AN 2007-391437, XP002749949, Dec. 27, 2006.

Medline Database, US National Library of Medicine (NLM), Liu Wei-Chung et al: "Cordyceps sinensis health supplement enhances recovery from taxol-induced leukopenia," Database accession No. NLM18367634, XP002749951, Apr. 2008.

Medline Database, US National Library of Medicine (NLM), Kaneko M et al: "Accelerated recovery from cyclophosphamide-induced leukopenia in mice administered a Japanese ethical herbal drug, Hochu-ekki-to", XP002749952, Database accession No. NLMI0598879, Nov. 1999.

Zhuang, S R, et al. "Effects of a Chinese 1-15 medical herbs complex on cellular immunity and toxicity-related conditions of breast cancer patients," The British Journal of Nutrition, vol. 107. No. 5 pp. 712-718 (2012).

Wei-Chung Liu, Experimental Biology and Medicine, vol. 233, No. 4, pp. 447-455 (2008).

First office action issued on Nov. 4, 2015 for counterpart Chinese Patent Application No. 201210169752.1.

Search report issued on Nov. 4, 2015 for counterpart Chinese Patent Application No. 201210169752.1.

Second Office Action issued on Jul. 5, 2016 for counterpart Chinese patent application No. 201210169752.1, along with the English translation.

Ponomariov, V.D. Ekstragirovanie lekarstvennogo syrya [Extraction of drug raw materials], Moscow, Medicina, pp. 115-120 (1976).

European Patent Application No. 13796295.7. Examination Report (Nov. 28, 2016).

Russian Patent Application No. 2014151160. Office Action (Oct. 14, 2016).

Third Office Action issued on Apr. 7, 2017 for counterpart Russian patent application No. 2014151160, along with the English translation; 13 pages.

Kaneko et al, "Accelerated recovery from cyclophosphamide-induced leukopenia in mice administered a Japanese ethical herbal drug, Hochu-ekki-to" Immunopharmacology, 1999; 44(3):223-31.

Liu et al, "Cordyceps sinensis health supplement enhances recovery from taxol-induced leukopenia", Exp Biol Med (Maywood) Apr. 2008, 233(4):447-55.

Ma et al, "Lanostane-type triterpenes from the sporoderm-broken spores of Ganoderma lucidum", The Journal of Antibiotics (2012) 65, 165-167.

Mok et al, "A double-blind placebo-controlled randomized study of Chinese herbal medicine as complementary therapy for reduction of chemotherapy-induced toxicity", Annals of Oncology, 2007, vol. 18, N4, 768-774.

* cited by examiner

APPLICATION OF COMPOSITION IN PREPARING HEALTH CARE PRODUCT OR MEDICINE FOR PREVENTING AND TREATING LEUKOPENIA CAUSED BY RADIOTHERAPY AND CHEMOTHERAPY

CROSS-REFERENCE TO RELATED APPLICATIONS

This application is the U.S. national stage of International Patent Application No. PCT/CN2013/000623, filed on May 27, 2013 and entitled APPLICATION OF COMPOSITION IN PREPARING HEALTH CARE PRODUCT OR MEDICINE FOR PREVENTING AND TREATING LEUKOPENIA CAUSED BY RADIOTHERAPY AND CHEMOTHERAPY, which claims the benefit of priority under 35 U.S.C. §119 from Chinese Patent Application No. 201210169752.1, filed May 29, 2012. The disclosures of the foregoing applications are incorporated herein by reference in their entirety.

TECHNICAL FIELD

The present invention relates to a composition for prevention and treatment of leucopenia induced by radiotherapy or chemotherapy and use of the composition.

BACKGROUND ART

Leucopenia refers to a condition where the absolute count of peripheral blood leucocytes is constantly less than $4.0 \times 10^9$/L. Cytotoxic drugs, toxic chemicals, and ionizing radiation, being the most common causes of decrease in neutrophils, may directly act on the stem cell pool and mitotic pool, impairing, damaging or suppressing hematopoietic stem cells/progenitor cells as well as early dividing cells. Some drugs may interfere with protein synthesis or cell division in a dose-dependant manner, while other drugs have dose-independent actions, possibly induced by allergic or immunological factors. Generally, patients with a slight decrease may mostly show primary symptoms, without clinically specific symptoms. Patients with a moderate or severe decrease are susceptible to infections and non-specific symptoms such as fatigue, weakness, dizziness, loss of appetite, etc. Leucopenia induced by radiotherapy or chemotherapy is the main reason why patients with malignant tumors often fail to complete the therapy. Administration of leukogenic drugs during an early stage of leucocyte decrease after radiotherapy or chemotherapy may substantially increase the number of leucocytes and allow patients to effectively and smoothly complete the chemotherapy and to improve their survival and quality of life, which represents a new approach to prevention and treatment of tumors. Patent Application CN101292742A discloses a pharmaceutical composition comprising *Ganoderma*, Radix Panacis Quinquefolii and fermented *Cordyceps sinensis* powder, which functions to enhance immunity. Patent Application CN102228252A discloses a composition of traditional Chinese medicines comprising Radix Panacis Quinquefolii and/or Radix Et Rhizoma Ginseng, *Ganoderma*, and fermented *Cordyceps sinensis* powder, which functions to alleviate physical fatigue. Patent Application CN102000129A discloses a pharmaceutical composition comprising Cordyceps polysaccharides or fermented *Cordyceps sinensis* powder, *Ganoderma*, and Radix Panacis Quinquefolii, which functions to enhance immunity. Up till now, no report or literature shows that a composition made from *Ganoderma*, Radix Panacis Quinquefolii or Radix Et Rhizoma Ginseng, fermented *Cordyceps sinensis* powder and/or Cordyceps has a function of preventing and treating leucopenia induced by radiotherapy or chemotherapy.

SUMMARY OF THE INVENTION

The objective of the present invention is to provide a composition for prevention and treatment of leucopenia induced by radiotherapy or chemotherapy and use thereof.

In accordance with the present invention, we select and combine raw materials *Ganoderma*, Radix Panacis Quinquefolii or Radix Et Rhizoma Ginseng, fermented *Cordyceps sinensis* powder and/or Cordyceps, and we surprisingly found that such a composition was capable of preventing and treating leucopenia induced by radiotherapy or chemotherapy.

The present invention provides a composition for prevention and treatment of leucopenia induced by radiotherapy or chemotherapy, which is made from raw materials including the following substances in parts by weight: 5 to 200 parts of *Ganoderma*, 5 to 150 parts of Radix Panacis Quinquefolii or Radix Et Rhizoma Ginseng, 1 to 90 parts of fermented *Cordyceps sinensis* powder and/or 1 to 120 parts of Cordyceps. The composition comprises the raw materials in parts by weight as above or consists of water and/or alcohol extracts of these raw materials as active components. Alternatively, the composition is obtained by water and/or alcohol extraction of a mixture of these raw materials, or consists of extracts as active components obtained by water and/or alcohol extraction of one or more of these raw materials.

Preferred are 20 to 120 parts of *Ganoderma*, 10 to 90 parts of Radix Panacis Quinquefolii or Radix Et Rhizoma Ginseng, 3 to 60 parts of fermented *Cordyceps sinensis* powder and/or 3 to 90 parts of Cordyceps.

More preferred are 40 parts of *Ganoderma*, 30 parts of Radix Panacis Quinquefolii or Radix Et Rhizoma Ginseng, 20 parts of fermented *Cordyceps sinensis* powder and/or 6.7 parts of Cordyceps.

The composition of the present invention may further comprise the following additional materials that do not compromise the efficacy of the present invention, or water and/or alcohol extracts of these additional materials, in parts by weight: one or more of 5 to 90 parts of Flos Rosae Rugosae, 5 to 150 parts of *Ganoderma* spore powder, 1 to 90 parts of *Ganoderma* spore oil, 10 to 400 parts of Radix Pseudostellariae, 1 to 120 parts of Folium Ginseng, 3 to 400 parts of Radix *Codonopsis* and 3 to 400 parts of Radix Astragali, or any combination thereof.

Preferred are one or more of 10 to 60 parts of Flos Rosae Rugosae, 10 to 120 parts of *Ganoderma* spore powder, 10 to 60 parts of *Ganoderma* spore oil, 20 to 200 parts of Radix Pseudostellariae, 20 to 90 parts of Folium Ginseng, 20 to 200 parts of Radix *Codonopsis* and 20 to 200 parts of Radix Astragali, or any combination thereof.

More preferred are one or more of 30 parts of Flos Rosae Rugosae, 30 parts of *Ganoderma* spore powder, 20 parts of *Ganoderma* spore oil, 40 parts of Radix Pseudostellariae, 30 parts of Folium Ginseng, 40 parts of Radix *Codonopsis* and 40 parts of Radix Astragali, or any combination thereof.

Most preferably, the composition of the present invention is a composition of 5 to 200 parts of *Ganoderma*, 5 to 150 parts of Radix Panacis Quinquefolii or Radix Et Rhizoma Ginseng, 1 to 90 parts of fermented *Cordyceps sinensis* powder and/or 1 to 120 parts of Cordyceps, and 5 to 90 parts of Flos Rosae Rugosae.

Preferably, the composition of the present invention is made from 20 to 120 parts of *Ganoderma*, 10 to 90 parts of Radix Panacis Quinquefolii or Radix Et Rhizoma Ginseng, 3 to 60 parts of fermented *Cordyceps sinensis* powder and/or 3 to 90 parts of Cordyceps, and 10 to 60 parts of Flos Rosae Rugosae.

Most preferably, the composition of the present invention is made from 40 parts of *Ganoderma*, 30 parts of Radix Panacis Quinquefolii or Radix Et Rhizoma Ginseng, 20 parts of fermented *Cordyceps sinensis* powder and/or 6.7 parts of Cordyceps, and 30 parts of Flos Rosae Rugosae.

In accordance with the present invention, Folium Ginseng, Radix Pseudostellariae, Radix *Codonopsis*, or Radix Astragali may be used instead of Radix Panacis Quinquefolii or Radix Et Rhizoma Ginseng, used in an amount the same as the amount in which they are additionally comprised in the composition of the present invention.

The term "*Ganoderma*", as used herein, refers to the dry sporocarp of fungal species *Ganoderma lucidum* (Leyss. ex Fr.) Karst. or *Ganoderma sinense* Zhao, Xu et Zhang of the family Polyporaceae. It has a sweet taste and a plain nature, is involved in the heart, lung, liver and kidney channels, and has the effects of nourishing physical strength and calming and tranquilizing the mind. The term "Radix Et Rhizoma Ginseng", as used herein, refers to the dry root and rootstock of the plant species *Panax ginseng* C. A. Mey. of the family Araliaceae. It may be various types of ginseng, such as garden ginseng, wild ginseng, dried fresh ginseng, dried fresh wild ginseng, sugar-processed ginseng, and red ginseng. The term Folium Ginseng refers to the dry leaves of the plant species *Panax ginseng* C. A. Mey. of the family Araliaceae. The term "Radix Panacis Quinquefolii", as used herein, also known as American ginseng, *huaqishen*, *yangshen*, or *guangdongshen*, refers to the dry root of the plant species *Panax quinquefolium* L. of the family Araliaceae. It has a sweet and slightly bitter taste and a cool nature, is involved in the heart, lung and kidney channels, and has the effects of invigorating Qi, nourishing Yin, clearing heat, and promoting fluid production. The term "Cordyceps", as used herein, refers to a dry complex from a dead body of an insect larva of the family Hepialidae and a stroma of the fungal species *Cordyceps sinensis* (Berk.) sace. of the family Clavicipitaceae parasitizing on the larva.

The term "fermented *Cordyceps sinensis* powder", as used herein, refers to a product of strains that were originally isolated from the natural Cordyceps of *Cordyceps sinensis* (Berk.) sace. and have been cultured under fermentation conditions, wherein the strains may be one of *Paecilomyces hepialli* Chen et Dai, sp.nov, *Hirsutella sinensis* Liu, Guo, Yu-et Zeng, sp.nov, *Cephalosporium sinensis* Chen sp.nov, *Mortiscrslla hepialid* C.T.&B.liu, *Paecilomyces sinensis* Chen, Xiao et Shi, sp.nov, *Tolypocladium sinensis* C.lan Li, *Cephalosporium sinens* Chen sp.nov, *Scytalidium hepialii* C.L.Li, *Chrysosporium sinens* Z.Q.liang, *Verticillium sinens* Wamg sp.nov, *Cephalosporium acremonium* Corda, Icones Fungorum, *Synnematium sinensis* Yin & Shen, *Isaria farinose* (Holmsk.) Fr. Systema Mycologicum, *Metarhizium anisopliae* (Metsch) Sorokin, *Hirsutella hepialid* Chen et Shen, *Sporothrix insectorum* de Hong & H. C. Evans, *Gliocladium roseum* (link) Thom, and *Mortierella* sp., or any combination thereof.

The strain from which the fermented *Cordyceps sinensis* powder from the present invention is derived is preferably one of *Paecilomyces* hepialli Chen et Dai, sp.nov, *Mortiscrslla hepialid* C.T.&B.liu, *Synnematium sinensis* Yin & Shen, *Gliocladium roseum* (link) Thom, *Mortierella* sp., *Cepha-losporium sinensis* Chen sp.nov or *Hirsutella sinensis* Liu, Guo, Yu-et Zeng, sp.nov, or any combination thereof.

The term "Flos Rosae Rugosae", as used herein, refers to the dry flower bud of the plant species *Rosa rugosa* Thumb or *Rose rugosacv* Plena of the family Rosaceae. It has a pungent, sweet and slightly bitter taste and a warm nature, and represents a warm-natured drug. Its most significant effects are to activate Qi flowing, resolve stagnation, harmonize the blood, and relieve pain.

The term "Radix *Codonopsis*" refers to the dry root of the plant species *Codonopsis pilosula* (Franch.) Nannf., *Codonopsis pilosula* Nannf.var.modesta (Nannf.) L. T. Shen, or *Codonopsis tangshen* Oliv. of the family Campanulaceae.

The term "Radix Pseudostellariae" used here in refers to the dry tuberous root of the plant species *Pseudostellaria heterophylla* (Miq.) Pax ex Pax et Hoffm. of the family Cargophyllaceae.

The term "Folium Ginseng" refers to the dry leaves of the plant species *Panax ginseng* C. A. Mey. of the family Araliaceae.

The term "Radix Astragali" refers to the dry root of the plant species *Astragalus membranaceus* (Fisch) Bge.var..mongholicus (Bge) Hsiao or *Astragalus membranaceus* (Fisch) Bge. of the family Fabaceae.

The *Ganoderma* spore powder according to the present invention is preferably sporoderm-broken *Ganoderma* spore powder.

The *Ganoderma* spore powder according to the present invention is sexual reproductive cells of *Ganoderma*, i.e., basidiospore powder.

The *Ganoderma* spore oil according to the present invention is a fatty lipid substance extracted from *Ganoderma* spore powder.

The alcohol according to the present invention is methanol or ethanol; the methanol may be at a concentration of 5 to 95%, and the ethanol may be at a concentration of 5 to 95%.

The composition according to the present invention can be prepared into any dosage form by adding an auxiliary agent or excipient acceptable in health care products, medicaments, or products.

The dosage form may be any one of a tablet, an oral liquid, a granule, a capsule, an electuary, a dripping pill, a pill, a powder, a lozenge, a fluid extract, an extract, an injection, and a syrup.

The present invention provides use of a composition comprising *Ganoderma*, Radix Panacis Quinquefolii or Radix Et Rhizoma Ginseng, fermented *Cordyceps sinensis* powder and/or Cordyceps, a composition made from raw materials comprising *Ganoderma*, Radix Panacis Quinquefolii or Radix Et Rhizoma Ginseng, fermented *Cordyceps sinensis* powder and/or Cordyceps, or a composition made from *Ganoderma*, Radix Panacis Quinquefolii or Radix Et Rhizoma Ginseng, fermented *Cordyceps sinensis* powder and/or Cordyceps, in the manufacture of a composition or a product for preventing and treating leucopenia induced by radiotherapy or chemotherapy.

The present invention further provides use of a composition comprising *Ganoderma*, Radix Panacis Quinquefolii or Radix Et Rhizoma Ginseng, fermented *Cordyceps sinensis* powder and/or Cordyceps and Flos Rosae Rugosae, a composition made from raw materials comprising *Ganoderma*, Radix Panacis Quinquefolii or Radix Et Rhizoma Ginseng, fermented *Cordyceps sinensis* powder and/or Cordyceps and Flos Rosae Rugosae, or a composition made from *Ganoderma*, Radix Panacis Quinquefolii or Radix Et Rhizoma Ginseng, fermented *Cordyceps sinensis* powder and/or Cordyceps and Flos Rosae Rugosae, in the manufacture of a composition or a product for preventing and treating leucopenia induced by radiotherapy or chemotherapy.

Provided is use of a composition prepared by adding any one or more components of Flos Rosae Rugosae, *Ganoderma* spore powder, *Ganoderma* spore oil, Radix Pseudostellariae, Folium Ginseng, Radix *Codonopsis*, and Radix Astragali to a composition comprising *Ganoderma*, Radix Panacis Quinquefolii or Radix Et Rhizoma Ginseng, fermented *Cordyceps sinensis* powder and/or Cordyceps, or to a composition made from raw materials comprising *Ganoderma*, Radix Panacis Quinquefolii or Radix Et Rhizoma Ginseng, fermented *Cordyceps sinensis* powder and/or Cordyceps, or to a composition made from *Ganoderma*, Radix Panacis Quinquefolii or Radix Et Rhizoma Ginseng, fermented *Cordyceps sinensis* powder and/or Cordyceps, in the manufacture of a composition or a product for preventing and treating leucopenia induced by radiotherapy or chemotherapy.

Provided is use of a composition prepared by adding any one or more components of *Ganoderma* spore powder, *Ganoderma* spore oil, Radix Pseudostellariae, Folium Ginseng, Radix *Codonopsis* and Radix Astragali to a composition comprising *Ganoderma*, Radix Panacis Quinquefolii or Radix Et Rhizoma Ginseng, fermented *Cordyceps sinensis* powder and/or Cordyceps and Flos Rosae Rugosae, or to a composition made from raw materials comprising *Ganoderma*, Radix Panacis Quinquefolii or Radix Et Rhizoma Ginseng, fermented *Cordyceps sinensis* powder and/or Cordyceps and Flos Rosae Rugosae, or to a composition made from *Ganoderma*, Radix Panacis Quinquefolii or Radix Et Rhizoma Ginseng, fermented *Cordyceps sinensis* powder and/or Cordyceps and Flos Rosae Rugosae, in the manufacture of a composition or a product for preventing and treating leucopenia induced by radiotherapy or chemotherapy.

A process for preparing the water and/or alcohol extracts of the raw materials for the traditional Chinese medicine composition according to the present invention comprises the steps of
1) weighing out traditional Chinese drugs as the raw materials; and
2) extracting the raw materials under reflux with alcohol or water to obtain a liquid extract as the active ingredient, and adding auxiliary agent(s) to prepare various dosage forms.

The process for preparing the water and/or alcohol extracts of the raw materials for the traditional Chinese medicine composition according to the present invention may comprise the steps of
1) weighing out traditional Chinese drugs as the raw materials, adding methanol or ethanol thereto to carry out extraction, recovering methanol or ethanol from the extraction liquid, to afford Extract I;
2) evaporating alcohol from the residual drugs, adding water to carry out extraction, to afford Extract II; and
3) combining Extract I and Extract II, carrying out filtration, concentrating the filtrate to an appropriate amount, adding pharmaceutically conventional auxiliary agent(s) to prepare a desired formulation by a pharmaceutically conventional process.

The process for preparing the water and/or alcohol extracts of the raw materials for the traditional Chinese medicine composition according to the present invention may comprise the steps of
1) raw material preparation: weighing out traditional Chinese drugs as the raw materials;
2) extraction and concentration: soaking the Chinese drug raw materials processed in step 1) in water, then decocting several times by heating, combining the liquid extracts to carry out filtration, concentrating the filtrate to an appropriate amount, cooling the concentrate and subjecting it to high-speed centrifugation to remove impurities, and reserving the product until use;
3) formulation preparation: preparing the concentrate obtained in step 2), alone or together with medicinally acceptable auxiliary agent(s), into a desired formulation by a pharmaceutically conventional process;
wherein, in step 2) above, the raw materials are soaked for 20 to 60 min, then decocted 1 to 3 times by heating for extraction, with each decoction lasting for 1 to 2 h and having a 6 to 13-fold amount of water added.

The composition for use in the manufacture of a composition or a product for preventing and treating leucopenia induced by radiotherapy or chemotherapy according to the present invention includes health care products and medicaments, wherein the term "product" includes those not encompassed in "health care products" or "medicaments", for example, essential oils, and pillows.

In order to provide a better understanding of the spirit of the present invention, animal experiments using the composition prepared from *Ganoderma*, Radix Panacis Quinquefolii or Radix Et Rhizoma Ginseng, fermented *Cordyceps sinensis* powder and/or Cordyceps and the composition prepared from *Ganoderma*, Flos Rosae Rugosae, Radix Panacis Quinquefolii or Radix Et Rhizoma Ginseng, fermented *Cordyceps sinensis* powder and/or Cordyceps, as well as the results thereof, are described hereinafter to demonstrate the effectiveness of the composition of the present invention in prevention and treatment of leucopenia induced by radiotherapy or chemotherapy.

Similarly, addition of any one or more of *Ganoderma* spore powder, *Ganoderma* spore oil, Ginseng, Radix Pseudostellariae, Radix *Codonopsis*, and Radix Astragali, or any combination thereof, can also lead to the same pharmacologic actions. Also, replacing Radix Panacis Quinquefolii or Radix Et Rhizoma Ginseng with Folium Ginseng, Radix Pseudostellariae, Radix *Codonopsis*, and/or Radix Astragali can lead to the same pharmacologic actions as well.

DETAILED DESCRIPTION

Example 1

1.5 kg Radix Panacis Quinquefolii, 2.0 kg *Ganoderma*, and 0.33 kg Cordyceps were weighed out. The Radix Panacis Quinquefolii and *Ganoderma* were sliced. The Cordyceps was pulverized and then put in a cloth bag. The above three drugs were soaked in water for 30 min, and decocted 3 times by heating. The first decoction lasted for 2 h with a 13-fold amount of water added, and the following decoctions each lasted for 1 h with a 10-fold amount of water added for each decoction. The three liquid extracts were combined and filtered. The filtrate was concentrated to produce a clear paste, which was then spray-dried to prepare a composite powder. The composition obtained, designated as Composition 1, was used in the efficacy experiments as below.

Example 2

1.5 kg Radix Panacis Quinquefolii, 2.0 kg *Ganoderma*, and 1.0 kg fermented *Cordyceps sinensis* powder were weighed out. The Radix Panacis Quinquefolii and *Gano-*

*derma* were sliced and the fermented *Cordyceps sinensis* powder was put in a cloth bag. The above three drugs were soaked in water for 30 min, and decocted 3 times by heating. The first decoction lasted for 2 h with a 13-fold amount of water added, and the following decoctions each lasted for 1 h with a 10-fold amount of water added for each decoction. The three liquid extracts were combined and filtered. The filtrate was concentrated to produce a clear paste, which was then spray-dried to prepare a composite powder. The composition obtained, Composition 2, was used in the efficacy experiments as below.

Example 3

1.5 kg Radix Panacis Quinquefolii, 2.0 kg *Ganoderma*, 1.0 kg fermented *Cordyceps sinensis* powder and 0.33 kg Cordyceps were weighed out. The Radix Panacis Quinquefolii and *Ganoderma* were sliced and the fermented *Cordyceps sinensis* powder was put in a cloth bag. The Cordyceps was pulverized and then put in a cloth bag. The above four drugs were soaked in water for 30 min, and decocted 3 times by heating. The first decoction lasted for 2 h with a 13-fold amount of water added, and the following decoctions each lasted for 1 h with a 10-fold amount of water added for each decoction. The three liquid extracts were combined and filtered. The filtrate was concentrated to produce a clear paste, which was then spray-dried to prepare a composite powder. The composition obtained, Composition 3, was used in the efficacy experiments as below.

Example 4

1.5 kg Radix Panacis Quinquefolii, 2.0 kg *Ganoderma*, 0.33 kg Cordyceps, and 1.5 kg Flos Rosae Rugosae were weighed out. The Radix Panacis Quinquefolii and *Ganoderma* were sliced. The Cordyceps was pulverized and then put in a cloth bag. The above four drugs were soaked in water for 30 min, and decocted 3 times by heating. The first decoction lasted for 2 h with a 13-fold amount of water added, and the following decoctions each lasted for 1 h with a 10-fold amount of water added for each decoction. The three liquid extracts were combined and filtered. The filtrate was concentrated to produce a clear paste, which was then spray-dried to prepare a composite powder. The composition obtained, Composition 4, was used in the efficacy experiments as below.

Example 5

1.5 kg Radix Panacis Quinquefolii, 2.0 kg *Ganoderma*, 1.0 kg fermented *Cordyceps sinensis* powder, and 1.5 kg Flos Rosae Rugosae were weighed out. The Radix Panacis Quinquefolii and *Ganoderma* were sliced and the fermented *Cordyceps sinensis* powder was put in a cloth bag. The above four drugs were soaked in water for 30 min, and decocted 3 times by heating. The first decoction lasted for 2 h with a 13-fold amount of water added, and the following decoctions each lasted for 1 h with a 10-fold amount of water added for each decoction. The three liquid extracts were combined and filtered. The filtrate was concentrated to produce a clear paste, which was then spray-dried to prepare a composite powder. The composition obtained, Composition 5, was used in the efficacy experiments as below.

Example 6

1.5 kg Radix Panacis Quinquefolii, 2.0 kg *Ganoderma*, 1.0 kg fermented *Cordyceps sinensis* powder, 0.33 kg Cordyceps and 1.5 kg Flos Rosae Rugosae were weighed out. The Radix Panacis Quinquefolii and *Ganoderma* were sliced and the fermented *Cordyceps sinensis* powder was put in a cloth bag. The Cordyceps was pulverized and then put in a cloth bag. The above five drugs were soaked in water for 30 min, and decocted 3 times by heating. The first decoction lasted for 2 h with a 13-fold amount of water added, and the following decoctions each lasted for 1 h with a 10-fold amount of water added for each decoction. The three liquid extracts were combined and filtered. The filtrate was concentrated to produce a clear paste, which was then spray-dried to prepare a composite powder. The composition obtained, Composition 6, was used in the efficacy experiments as below.

Example 7

300 g Radix Panacis Quinquefolii, 400 g *Ganoderma*, 200 g fermented *Cordyceps sinensis* powder (*Hirsutella sinensis* Liu, Guo, Yu-et Zeng, sp.nov), and 300 g Flos Rosae Rugosae were weighed out. The Radix Panacis Quinquefolii and *Ganoderma* were sliced, and the fermented *Cordyceps sinensis* powder was put in a cloth bag. The above four drugs were soaked in water for 20 min, and decocted 3 times by heating. Each decoction lasted for 1 h with a 10-fold amount of water added. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 8

300 g Radix Panacis Quinquefolii, 400 g *Ganoderma*, 67 g Cordyceps, 200 g fermented *Cordyceps sinensis* powder (*Paecilomyces hepialli* Chen et Dai, sp.nov), and 300 g Flos Rosae Rugosae were weighed out. The Radix Panacis Quinquefolii and *Ganoderma* were sliced, and the fermented *Cordyceps sinensis* powder was put in a cloth bag. The Cordyceps was pulverized and then put in a cloth bag. The above five drugs were soaked in water for 1 h, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for tablets were added thereto and uniformly mixed, and a 20,000 ml oral liquid was prepared by conventional processes for tablets.

Example 9

150 g Radix Panacis Quinquefolii, 90 g fermented *Cordyceps sinensis* powder (*Hirsutella hepialid* Chen et Shen), 120 g Cordyceps, 200 g *Ganoderma*, and 90 g Flos Rosae Rugosae were weighed out. The Radix Panacis Quinquefolii and *Ganoderma* were sliced, and the fermented *Cordyceps sinensis* powder was put in a cloth bag. The above four drugs were soaked in water for 1 h, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 10

500 g Radix Et Rhizoma Ginseng, 100 g fermented *Cordyceps sinensis* powder (*Synnematium sinensis* Yin & Shen), 500 g *Ganoderma*, and 500 g Flos Rosae Rugosae were weighed out. The Radix Et Rhizoma Ginseng and *Ganoderma* were sliced, and the fermented *Cordyceps sinensis* powder and Flos Rosae Rugosae were put in a cloth bag. The above four drugs were soaked in water for 30 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 11

500 g Radix Panacis Quinquefolii, 100 g fermented *Cordyceps sinensis* powder (*Hirsutella sinensis* Liu, Guo, Yu-et Zeng, sp.nov), 500 g *Ganoderma*, and 500 g Flos Rosae Rugosae were weighed out. The Radix Panacis Quinquefolii and *Ganoderma* were sliced, and the fermented *Cordyceps sinensis* powder and Flos Rosae Rugosae were put in a cloth bag. The above four drugs were soaked in water for 20 min, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 12

150 g Radix Panacis Quinquefolii, 120 g Cordyceps, 200 g *Ganoderma*, and 90 g Flos Rosae Rugosae were weighed out. The Radix Panacis Quinquefolii and *Ganoderma* were sliced. The Cordyceps was pulverized and then put in a cloth bag. The above four drugs were soaked in water for 40 min, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 13

150 g Radix Et Rhizoma Ginseng, 90 g fermented *Cordyceps sinensis* powder (*Gliocladium roseum* (link) Thom), 200 g *Ganoderma*, and 90 g Flos Rosae Rugosae were weighed out. The Radix Et Rhizoma Ginseng and *Ganoderma* were sliced, and the fermented *Cordyceps sinensis* powder was put in a cloth bag. The above four drugs were soaked in water for 1 h, and decocted twice by heating. The first decoction lasted for 2 h with a 15-fold amount of water added, and the second decoction lasted for 1.5 h with a 10-fold amount of water added. The two liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 14

150 g Radix Panacis Quinquefolii, 90 g fermented *Cordyceps sinensis* powder (*Hirsutella hepialid* Chen et Shen), 120 g Cordyceps, 200 g *Ganoderma*, and 90 g Flos Rosae Rugosae were weighed out. The Radix Panacis Quinquefolii and *Ganoderma* were sliced, and the fermented *Cordyceps sinensis* powder was put in a cloth bag. The above four drugs were soaked in water for 1 h, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 15

100 g Radix Panacis Quinquefolii, 30 g Cordyceps, 200 g *Ganoderma*, and 100 g Flos Rosae Rugosae were weighed out. The Radix Panacis Quinquefolii and *Ganoderma* were sliced. The Cordyceps was pulverized and then put in a cloth bag. The above four drugs were soaked in water for 30 min, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 16

150 g Radix Panacis Quinquefolii, 30 g fermented *Cordyceps sinensis* powder (*Hirsutella sinensis* Liu, Guo, Yu-et Zeng, sp.nov), 200 g *Ganoderma*, and 100 g Flos Rosae Rugosae were weighed out. The Radix Panacis Quinquefolii and *Ganoderma* were sliced, and the fermented *Cordyceps sinensis* powder was put in a cloth bag. The above four drugs were soaked in water for 1 h, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 17

90 g Radix Panacis Quinquefolii, 90 g Cordyceps, 120 g *Ganoderma*, and 60 g Flos Rosae Rugosae were weighed out. The Radix Panacis Quinquefolii and *Ganoderma* were sliced. The Cordyceps was pulverized and then put in a cloth bag. The above four drugs were soaked in water for 20 min, and decocted 3 times by heating. Each decoction lasted for 1 h with a 10-fold amount of water added for each. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 18

90 g Radix Et Rhizoma Ginseng, 90 g Cordyceps, 120 g *Ganoderma*, and 60 g Flos Rosae Rugosae were weighed out. The Radix Et Rhizoma Ginseng and *Ganoderma* were sliced. The Cordyceps was pulverized and then put in a cloth bag. The above four drugs were soaked in water for 30 min, and decocted 3 times by heating. Each decoction lasted for 1 h with a 10-fold amount of water added for each. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 19

90 g Radix Panacis Quinquefolii, 60 g fermented *Cordyceps sinensis* powder (*Cephalosporium sinensis* Chen sp.nov), 120 g *Ganoderma*, and 60 g Flos Rosae Rugosae were weighed out. The Radix Panacis Quinquefolii and *Ganoderma* were sliced, and the fermented *Cordyceps sinensis* powder was put in a cloth bag. The above four drugs were soaked in water for 20 min, and decocted 3 times by heating. Each decoction lasted for 1 h with a 10-fold amount of water added for each. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 20

300 g Radix Panacis Quinquefolii, 400 g *Ganoderma*, 67 g Cordyceps, and 300 g Flos Rosae Rugosae were weighed out. The Radix Panacis Quinquefolii and *Ganoderma* were sliced. The Cordyceps was pulverized and then put in a cloth bag. The above four drugs were soaked in water for 1 h, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for tablets were added thereto and uniformly mixed; and various types of tablets were prepared by conventional processes for tablets.

Example 21

300 g Radix Panacis Quinquefolii, 400 g *Ganoderma*, 200 g fermented *Cordyceps sinensis* powder (*Paecilomyces hepialli* Chen et Dai, sp.nov), and 300 g Flos Rosae Rugosae were weighed out. The Radix Panacis Quinquefolii and *Ganoderma* were sliced, and the fermented *Cordyceps sinensis* powder was put in a cloth bag. The above four drugs were soaked in water for 20 min, and decocted 3 times by heating. Each decoction lasted for 1 h with a 10-fold amount of water added for each. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 22

500 g Radix Panacis Quinquefolii, 100 g Cordyceps, 500 g *Ganoderma*, 500 g Flos Rosae Rugosae and 500 g sporoderm-broken *Ganoderma* spore powder were weighed out. The Radix Panacis Quinquefolii and *Ganoderma* were sliced. The Cordyceps was pulverized and then put in a cloth bag. The above four drugs were soaked in water for 20 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for tablets and the sporoderm-broken *Ganoderma* spore powder were added thereto and uniformly mixed; and various types of tablets were prepared by conventional processes for tablets.

Example 23

500 g Radix Et Rhizoma Ginseng, 100 g fermented *Cordyceps sinensis* powder (*Paecilomyces sinensis* Chen, Xiao et Shi, sp.nov), 500 g *Ganoderma*, 500 g Flos Rosae Rugosae and 500 g sporoderm-broken *Ganoderma* spore powder were weighed out. The Radix Et Rhizoma Ginseng and *Ganoderma* were sliced, and the fermented *Cordyceps sinensis* powder and the sporoderm-broken *Ganoderma* spore powder were put in a cloth bag. The above five drugs were soaked in water for 20 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for granules were added thereto and uniformly mixed; and granules were prepared by conventional processes for granules.

Example 24

150 g Radix Panacis Quinquefolii, 90 g fermented *Cordyceps sinensis* powder (*Tolypocladium sinensis* C.lan Li), 200 g *Ganoderma,* 90 g Flos Rosae Rugosae and 150 g sporoderm-broken *Ganoderma* spore powder were weighed out. The Radix Panacis Quinquefolii and *Ganoderma* were sliced, and the fermented *Cordyceps sinensis* powder was put in a cloth bag. The above four drugs were soaked in water for 20 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for tablets and the *Ganoderma* spore powder were added thereto and uniformly mixed; and various types of tablets were prepared by conventional processes for tablets.

Example 25

500 g Radix Panacis Quinquefolii, 100 g Cordyceps, 500 g *Ganoderma,* 500 g Flos Rosae Rugosae and 100 g *Ganoderma* spore oil were weighed out. The Radix Panacis Quinquefolii and *Ganoderma* were sliced, and the Cordyceps was pulverized. Upon addition of 80% ethanol, the above four drugs were extracted twice under reflux, with each extraction lasting for 2 h, and then filtered. Ethanol was recovered from the liquid filtrate until no ethanol odor could be smelled. A paste was made by further concentration under reduced pressure, or fine particles were made by spray drying; auxiliary agents frequently used for dripping pills and the *Ganoderma* spore oil were added thereto and uniformly mixed; and dripping pills were prepared by conventional processes for dripping pills.

Example 26

500 g Radix Panacis Quinquefolii, 100 g fermented *Cordyceps sinensis* powder (*Synnematium sinensis* Yin & Shen), 500 g *Ganoderma,* 500 g Flos Rosae Rugosae, 500 g sporoderm-broken *Ganoderma* spore powder, 100 g *Ganoderma* spore oil and 100 g Folium Ginseng were weighed out. The Radix Panacis Quinquefolii and *Ganoderma* were sliced, and the fermented *Cordyceps sinensis* powder was put in a cloth bag. The above drugs were soaked in water for 40 min, and decocted 3 times by heating. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for granules, the sporoderm-broken *Ganoderma* spore powder and the *Ganoderma* spore oil were added thereto and uniformly mixed; and granules were prepared by conventional processes for granules.

Example 27

150 g Radix Panacis Quinquefolii, 90 g fermented *Cordyceps sinensis* powder (*Hirsutella hepialid* Chen et Shen), 200 g *Ganoderma,* 90 g Flos Rosae Rugosae and 400 g Radix *Codonopsis* were weighed out. The Radix Panacis Quinquefolii, *Ganoderma* and Radix *Codonopsis* were sliced, and the fermented *Cordyceps sinensis* powder was put in a cloth bag. The above five drugs were soaked in water for 40 min, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for tablets were added thereto and uniformly mixed; and various types of tablets were prepared by conventional processes for tablets.

Example 28

150 g Radix Panacis Quinquefolii, 120 g Cordyceps, 200 g *Ganoderma,* 90 g Flos Rosae Rugosae and 400 g Radix Astragali were weighed out. The Radix Panacis Quinquefolii, *Ganoderma* and Radix Astragali were sliced. The Cordyceps was pulverized and then put in a cloth bag. The above five drugs were soaked in water for 20 min, and decocted 3 times by heating. The first decoction lasted for 2 h, and the following decoctions each lasted for 1 h, with a 14-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agents frequently used for lozenges were added thereto and uniformly mixed, and lozenges were prepared by conventional processes for lozenges.

Example 29

500 g Radix Panacis Quinquefolii, 50 g fermented *Cordyceps sinensis* powder (*Paecilomyces hepialli* Chen et Dai, sp.nov), 50 g fermented *Cordyceps sinensis* powder (*Hirsutella sinensis* Liu, Guo, Yu-et Zeng, sp.nov), 500 g *Ganoderma,* 500 g Flos Rosae Rugosae and 300 g Radix *Codonopsis* were weighed out. The Radix Panacis Quinquefolii, *Ganoderma* and Radix *Codonopsis* were sliced, and the fermented *Cordyceps sinensis* powders were put in a cloth bag. The above five drugs were soaked in water for 1 h, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for powder were added thereto and uniformly mixed; and powder was prepared by conventional processes for powder.

Example 30

500 g Radix Panacis Quinquefolii, 100 g Cordyceps, 500 g *Ganoderma*, 500 g Flos Rosae Rugosae and 300 g Radix Astragali were weighed out. The Radix Panacis Quinquefolii, *Ganoderma* and Radix Astragali were sliced. The *Cordyceps* was pulverized and then put in a cloth bag. The above five drugs were soaked in water for 20 min, and decocted 3 times by heating. The first decoction lasted for 2 h, and the following decoctions each lasted for 1 h, with a 14-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 31

100 g Radix Panacis Quinquefolii, 200 g *Ganoderma*, 30 g *Cordyceps*, 3 g fermented *Cordyceps sinensis* powder (Cs-C-Q80 *Hirsutella sinensis* Liu, Guo, Yu-et Zeng, sp.nov), 100 g Flos Rosae Rugosae and 100 g *Ganoderma* spore powder were weighed out. The Radix Panacis Quinquefolii and *Ganoderma* were sliced, and the *Cordyceps* was pulverized and put in a cloth bag together with the *Ganoderma* spore powder. The above five drugs were soaked in water for 20 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for tablets were added thereto and uniformly mixed; and various types of tablets were prepared by conventional processes for tablets.

Example 32

100 g Radix Panacis Quinquefolii, 200 g *Ganoderma*, 30 g fermented *Cordyceps sinensis* powder (*Mortiscrslla hepialid* C.T.& B.liu), 100 g Flos Rosae Rugosae and 100 g *Ganoderma* spore powder were weighed out. The Radix Panacis Quinquefolii and *Ganoderma* were sliced, and the fermented *Cordyceps sinensis* powder and the *Ganoderma* spore powder were put in a cloth bag. The above five drugs were soaked in water for 20 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for pills were added thereto and uniformly mixed; and various types of pills were prepared by conventional processes for pills.

Example 33

90 g Radix Panacis Quinquefolii, 120 g *Ganoderma*, 90 g *Cordyceps*, 60 g Flos Rosae Rugosae and 90 g *Ganoderma* spore oil were weighed out. The Radix Panacis Quinquefolii and *Ganoderma* were sliced. The *Cordyceps* was pulverized and then put in a cloth bag. The above four drugs were soaked in water for 30 min, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for granules and the *Ganoderma* spore oil were added thereto and uniformly mixed; and granules were prepared by conventional processes for granules.

Example 34

100 g Radix Panacis Quinquefolii, 200 g *Ganoderma*, 30 g *Cordyceps*, 100 g Flos Rosae Rugosae and 200 g Radix Pseudostellariae were weighed out. The Radix Panacis Quinquefolii and *Ganoderma* were sliced, and the *Cordyceps* was pulverized and then put in a cloth bag. The above five drugs were soaked in water for 40 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, auxiliary agents frequently used for soft extracts were added thereto and uniformly mixed, and a soft extract was prepared by conventional processes for soft extracts.

Example 35

100 g Radix Panacis Quinquefolii, 200 g *Ganoderma*, 30 g *Cordyceps*, 100 g Flos Rosae Rugosae and 200 g Folium Ginseng were weighed out. The Radix Panacis Quinquefolii and *Ganoderma* were sliced, and the *Cordyceps* was pulverized and then put in a cloth bag. The above five drugs were soaked in water for 40 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agents frequently used for syrups were added thereto and uniformly mixed, and a syrup was prepared by conventional processes for syrups.

Example 36

100 g Radix Panacis Quinquefolii, 200 g *Ganoderma*, 30 g fermented *Cordyceps sinensis* powder (*Mortierella* sp.), 100 g Flos Rosae Rugosae and 200 g Radix *Codonopsis* were weighed out. The Radix Panacis Quinquefolii, *Ganoderma* and Radix *Codonopsis* were sliced, and the fermented *Cordyceps sinensis* powder was put in a cloth bag. The above five drugs were soaked in water for 40 min, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fined particles were made by spray drying; auxiliary agents frequently used for tablets were added thereto and uniformly mixed; and various types of tablets were prepared by conventional processes for tablets.

Example 37

100 g Radix Panacis Quinquefolii, 200 g *Ganoderma*, 30 g fermented *Cordyceps sinensis* powder (*Verticillium sinens* Wamg sp.nov), 100 g Flos Rosae Rugosae and 200 g Radix Astragali were weighed out. The Radix Panacis Quinquefolii, *Ganoderma* and Radix Astragali were sliced, and the fermented *Cordyceps sinensis* powder was put in a cloth bag. The above five drugs were soaked in water for 40 min, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for capsules were added thereto and uniformly mixed; and capsules were prepared by conventional processes for capsules.

Example 38

90 g Radix Panacis Quinquefolii, 120 g *Ganoderma*, 30 g fermented *Cordyceps sinensis* powder (*Cephalosporium sinensis* Chen sp.nov), 30 g fermented *Cordyceps sinensis* powder (*Synnematium sinensis* Yin & Shen), 60 g Flos Rosae Rugosae and 60 g *Ganoderma* spore oil were weighed out. The Radix Panacis Quinquefolii and *Ganoderma* were sliced, and the fermented *Cordyceps sinensis* powders were put in a cloth bag. The above four drugs were soaked in water for 1 h, and decocted 3 times by heating. The first decoction lasted for 2 h, and the following decoctions each lasted for 1 h, with a 13-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for pills and the *Ganoderma* spore oil were added thereto and uniformly mixed; and various types of pills were prepared by conventional processes for pills.

Example 39

90 g Radix Panacis Quinquefolii, 120 g *Ganoderma*, 90 g *Cordyceps*, 60 g Flos Rosae Rugosae, 200 g Radix Astragali, and 10 g *Ganoderma* spore oil were weighed out. The Radix Panacis Quinquefolii, *Ganoderma* and Radix Astragali were sliced, and the *Cordyceps* was pulverized and then put in a cloth bag. The above five drugs were soaked in water for 40 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agents frequently used for syrups were added thereto and uniformly mixed, and a syrup was prepared by conventional processes for syrups.

Example 40

300 g Radix Panacis Quinquefolii, 400 g *Ganoderma*, 200 g fermented *Cordyceps sinensis* powder (*Scytalidium hepialii* C.L.Li), 300 g Flos Rosae Rugosae and 400 g *Ganoderma* spore powder were weighed out. The Radix Panacis Quinquefolii and *Ganoderma* were sliced, and the *Cordyceps* was pulverized and then put in a cloth bag. The above four drugs were soaked in water for 20 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for tablets and the *Ganoderma* spore powder were added thereto and uniformly mixed; and various types of tablets were prepared by conventional processes for tablets.

Example 41

300 g Radix Panacis Quinquefolii, 400 g *Ganoderma*, 67 g *Cordyceps*, 300 g Flos Rosae Rugosae and 20 g *Ganoderma* spore oil were weighed out. The Radix Panacis Quinquefolii and *Ganoderma* were sliced, and the *Cordyceps* was pulverized and then put in a cloth bag. The above four drugs were soaked in water for 30 min, and decocted 3 times by heating. The first decoction lasted for 2 h, and the following decoctions each lasted for 1 h with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for granules and the *Ganoderma* spore oil were added thereto and uniformly mixed; and granules were prepared by conventional processes for granules.

Example 42

300 g Radix Panacis Quinquefolii, 400 g *Ganoderma*, 200 g fermented *Cordyceps sinensis* powder (*Cephalosporium sinens* Chen sp.nov), 300 g Flos Rosae Rugosae and 400 g Radix Pseudostellariae were weighed out. The Radix Panacis Quinquefolii and *Ganoderma* were sliced, and the fermented *Cordyceps sinensis* powder was put in a cloth bag. The above five drugs were soaked in water for 40 min, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fined particles were made by spray drying; auxiliary agents frequently used for tablets were added thereto and uniformly mixed; and various types of tablets were prepared by conventional processes for tablets.

Example 43

300 g Radix Panacis Quinquefolii, 400 g *Ganoderma*, 67 g *Cordyceps*, 300 g Flos Rosae Rugosae and 400 g Radix Pseudostellariae were weighed out. The Radix Panacis Quinquefolii and *Ganoderma* were sliced, and the *Cordyceps* was pulverized and then put in a cloth bag. The above five drugs were soaked in water for 40 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agents frequently used for syrups were added thereto and uniformly mixed, and a syrup was prepared by conventional processes for syrups.

Example 44

300 g Radix Panacis Quinquefolii, 400 g *Ganoderma*, 100 g fermented *Cordyceps sinensis* powder (*Chrysosporium sinens* Z.Q.liang), 100 g fermented *Cordyceps sinensis* powder (*Hirsutella sinensis* Liu, Guo, Yu-et Zeng, sp.nov), and 300 g Flos Rosae Rugosae were weighed out. The Radix Panacis Quinquefolii and *Ganoderma* were sliced, and the fermented *Cordyceps sinensis* powders were put in a cloth bag. Upon addition of 5% methanol, the drugs were extracted twice under reflux, with each extraction lasting for 1 h. Then the liquid extracts were combined, and methanol was recovered to obtain an alcohol extract. The residual drugs were further decocted twice in water by heating. The first decoction lasted for 2 h, and the following decoction lasted for 1 h, with a 10-fold amount of water added for each decoction. The alcohol extract and water extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for granules were added thereto and uniformly mixed; and granules were prepared by conventional processes for granules.

Example 45

300 g Radix Panacis Quinquefolii, 400 g *Ganoderma*, 67 g *Cordyceps*, 20 g fermented *Cordyceps sinensis* powder (*Hirsutella sinensis* Liu, Guo, Yu-et Zeng, sp.nov), and 300 g Flos Rosae Rugosae were weighed out. The Radix Panacis Quinquefolii and *Ganoderma* were sliced, and the *Cordyceps* was pulverized and then put in a cloth bag. Upon addition of 75% ethanol, the drugs were extracted for 2 h under reflux, and ethanol was recovered to obtain an alcohol extract. The residual drugs were further decocted three times in water by heating, with each decoction lasting for 2 h. The alcohol extract and water extracts were combined and filtered, the liquid filtrate was concentrated to an appropriate level, the liquid concentrate was left to cool down, and the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 46

300 g Radix Et Rhizoma Ginseng, 400 g *Ganoderma*, 200 g fermented *Cordyceps sinensis* powder (*Cephalosporium acremonium* Corda, Icones Fungorum), 300 g Flos Rosae Rugosae and 400 g Radix *Codonopsis* were weighed out. The Radix Et Rhizoma Ginseng, *Ganoderma* and Radix *Codonopsis* were sliced, and the fermented *Cordyceps sinensis* powder was put in a cloth bag. Upon addition of 95% methanol, the drugs were extracted twice under reflux, with each extraction lasting for 1 h. Then the liquid extracts were combined, and methanol was recovered to obtain an alcohol extract. The residual drugs were further decocted 3 times in water by heating. The first decoction lasted for 2 h, and the following decoctions each lasted for 1 h, with a 10-fold amount of water added for each decoction. The alcohol extract and water extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for granules were added thereto and uniformly mixed; and granules were prepared by conventional processes for granules.

Example 47

300 g Radix Et Rhizoma Ginseng, 400 g *Ganoderma*, 200 g fermented *Cordyceps sinensis* powder (*Sporothrix insectorum* de Hong & H. C. Evans), 300 g Flos Rosae Rugosae and 400 g Radix *Codonopsis* were weighed out. The Radix Et Rhizoma Ginseng and *Ganoderma* were sliced, and the *Cordyceps* was pulverized and put in a cloth bag. Upon addition of 95% ethanol, the drugs were extracted under reflux for 2 h, and ethanol was recovered to obtain an alcohol extract. The residual drugs were further decocted 3 times in water by heating, with each decoction lasting for 2 h. The alcohol extract and water extracts were combined and filtered, the liquid filtrate was concentrated to an appropriate level, the liquid concentrate was left to cool down, and the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 48

300 g Radix Et Rhizoma Ginseng, 400 g *Ganoderma*, 67 g *Cordyceps*, 300 g Flos Rosae Rugosae, 300 *Ganoderma* spore powder and 400 g Radix Astragali were weighed out. The Radix Et Rhizoma Ginseng and *Ganoderma* were sliced, and the *Cordyceps* was pulverized and then put in a cloth bag. Upon addition of 5% ethanol, the drugs were extracted under reflux for 2 h, and ethanol was recovered to obtain an alcohol extract. The residual drugs were further decocted twice in water by heating, with each decoction lasting for 2 h. The alcohol extract and water extracts were combined and filtered, the liquid filtrate was concentrated to an appropriate level, the liquid concentrate was left to cool down, and the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 49

300 g Radix Panacis Quinquefolii, 400 g *Ganoderma*, 200 g fermented *Cordyceps sinensis* powder (*Isaria farinose* (Holmsk.) Fr. Systema Mycologicum), 300 g Flos Rosae Rugosae and 400 g Radix Astragali were weighed out. The Radix Panacis Quinquefolii and *Ganoderma* were sliced, and the fermented *Cordyceps sinensis* powder was put in a cloth bag. Upon addition of 95% methanol, the drugs were extracted twice under reflux for 2 h, with each extraction lasting for 1 h. Then the liquid extracts were combined, and methanol was recovered to obtain an alcohol extract. The residual drugs were further decocted 3 times in water by heating. The first decoction lasted for 2 h, and the following decoctions each lasted for 1 h, with a 10-fold amount of water added for each decoction. The alcohol extract and water extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for granules were added thereto and uniformly mixed; and granules were prepared by conventional processes for granules.

Example 50

300 g Radix Panacis Quinquefolii, 400 g *Ganoderma*, 67 g *Cordyceps*, 300 g Flos Rosae Rugosae, and 90 g Folium Ginseng were weighed out. The Radix Panacis Quinquefolii and *Ganoderma* were sliced, and the *Cordyceps* was pulverized and then put in a cloth bag. Upon addition of 5% ethanol, the drugs were extracted under reflux for 2 h, and ethanol was recovered to obtain an alcohol extract. The residual drugs were further decocted 3 times in water by heating, with each decoction lasting for 2 h. The alcohol extract and water extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 51. Animal Experiment Report of Composition 1 of Example 1 in Prevention and Treatment of Leucopenia Induced by Radiotherapy or Chemotherapy 1. Materials and Methods
1.1 Sources of Samples The test drug was Composition 1 (Radix Panacis Quinquefolii, *Ganoderma*, and *Cordyceps*) provided by Jiangzhong Pharmaceutical Co. Ltd. as composite powder. 1 g dry composite powder was equivalent to 10.97 g total crude drugs.
1.2 Laboratory Animals Male and female mice of Kunming breed, each weighing 18 to 22 g, were provided by the Laboratory Animal Center, Jiangxi University of Traditional Chinese Medicine (Animal Certification Number: SCXK (Jiangxi) 2005-0001).
1.3 Primary Reagents Drug for positive control, batyl alcohol (100 mg/kg), was obtained from Shanghai Sine Yanan Pharmaceutical Co., Ltd. (batch No. 20080723). Cyclophosphamide was manufactured by Jiangsu Hengrui Medicine Co., Ltd. (batch No. 08110621). Cytarabine was manufactured by Shanghai Hualian Pharmaceuticals (batch No. 0512048). EDTA-$K_2$ was manufactured by Sinopharm Chemical Reagent Co., Ltd. (batch No. F20080423).
1.4 Primary Instruments Sysmex-2000iV blood cell analyzer (Sysmex Corporation, Japan), AR1140/C eletronic analytic balance (Ohaus (Shanghai) Corp.), microscope (Olympus), pipets (Gilson), and ELx800 Absorbance reader for ELISA (BioTek, US).
2. Experimental Methods
2.1 Effect of Composition 1 on Leucocyte Reduction in Mice Induced by Cyclophosphamide[1]
2.1.1 Grouping, Modeling and Dosage Regime Mice were randomly divided into 6 groups with 10 animals per group, i.e., normal control group, model control group, positive control group, and groups on low, medium and high doses of Composition 1. The low-, medium- and high-dose groups were intragastrically given Composition 1 at a dose of 2.0 g crude drug/kg, 4.0 g crude drug/kg, and 12.0 g crude drug/kg, respectively; the positive control group was intragastrically given batyl alcohol (100 mg/kg) at a dose of 0.1 ml/10 g body weight; the normal control group and the model control group were intragastrically given an equivalent volume of distilled water; and the dosage regime lasted for 15 days with one dose per day. From day 9 of intragastrical administration, all mice in each group, except the normal control group, were given cyclophosphamide at a dose of 40 mg/kg each day via subcutaneous injection for 3 consecutive days. One hour after the intragastrical administration on day 15, blood and femurs were harvested for tests.
2.1.2 Peripheral Leucocyte Assay 40 μL blood was drawn from the tail vein of the mice and transferred into a EDTA-$K_2$ anticoagulative tube, into which 160 μL dilution liquid was added, and then assayed in an automatic blood cell analyzer.
2.1.3 Bone Marrow Nucleated Cell Count (BMC)

Mice were sacrificed by cervical dislocation. The left femur was removed and flushed with a 10 ml solution of 3% acetic acid to obtain the cells in the bone marrow. The number of cells in 4 large grids on a hemacytometer was counted, and the number was multiplied by $2.5 \times 10^4$ to obtain the BMC in one femur.

2.1.4 Bone Marrow DNA Content Determination

A 7 mm section was dissected from the middle of the right femur. The whole bone marrow was flushed into a centrifuge tube with a 10 mL solution of 0.005 mol/L $CaCl_2$, placed in a refrigerator at 4° C. for 30 min, and then centrifuged at 2500 r/min for 15 min. The supernatant was discarded, and a 5 ml solution of 0.2 mol/L $HClO_4$ was added to the precipitate and uniformly mixed. The mixture was heated in a water bath at 90° C. for 15 min, then kept in a refrigerator overnight, and centrifuged at 2500 r/min for 10 min. The supernatant was removed and its absorbance at 268 nm was measured.

2.2 Effect of Composition 1 on Leucocyte Reduction in Mice Induced by Cytarabine[2]

2.2.1 Grouping, Modeling and Dosage Regime

The grouping and dosage regime were the same as those in 2.1.1, except that, from day 7 of intragastrical administration, all animals in each group, except the normal control group, were given cytarabine at a dose of 100 mg/kg via peritoneal injection for 2 consecutive days, and from the next day the dose was switched to 50 mg/kg which was continued for another 3 consecutive days. One hour after the intragastrical administration on day 15, blood and femurs were harvested for tests.

2.2.2 Peripheral Leucocyte Assay, Bone Marrow Nucleated Cell Count, and Bone Marrow DNA Content Determination All the same as in 2.1.

2.3 Effect of Composition 1 on Leucocyte Reduction in Mice Induced by X-Ray Radiation[3]

2.3.1 Grouping, Modeling and Dosage Regime

The grouping and dosage regime were the same as those in 2.1.1 except that all groups other than the normal group were subjected to systematic radiation once under low-energy X ray from a medical linear accelerator to establish models, wherein the skin-to-source distance was 100 cm, the radiation dose was 4.0 Gy/min and the radiation duration was 4 min One hour after the intragastrical administration on day 8 and day 15, blood and femurs were harvested for tests.

2.3.2 Peripheral Leucocyte Assay, Bone Marrow Nucleated Cell Count, and Bone Marrow DNA Content Determination All the same as in 2.1.

2.4 Statistic Method

Data was processed by SPSS15.0 using a one-way ANOVA analysis. P<0.05 is considered as significant difference. P<0.01 is considered as highly significant difference.

3. Results 3.1 Effect of Composition 1 on Leucocyte Reduction in Mice Induced by Cyclophosphamide Test results are shown in Tables 1 and 2. The number of peripheral WBC and the contents of bone marrow nucleated cells and DNA in the model control group decreased as compared to those in the normal control group, suggesting a successful modeling. Compared to the model control group, the number of peripheral WBC and the contents of bone marrow nucleated cells and DNA significantly increased in the Composition 1 high- and medium-dose groups and in the positive control group, and also showed a tendency to increase in the Composition 1 low-dose group, indicating that Composition 1 can resist leucocyte reduction in mice induced by cyclophosphamide and improve the hematopoietic function of the bone marrow thereof.

TABLE 1

Effect of Composition 1 on peripheral leucocyte reduction in mice induced by cyclophosphamide ($\bar{x} \pm s$, $\times 10^9$)

| Groups | Dose (g crude drug/kg) | Number of animals | WBC before modeling | WBC after modeling | WBC after treatment |
|---|---|---|---|---|---|
| Normal control group | 0.0 | 10 | 8.19 ± 1.96 | 8.37 ± 1.54 | 8.28 ± 1.77 |
| Model control group | 0.0 | 10 | 8.08 ± 1.58 | 3.46 ± 1.09** | 4.25 ± 1.41** |
| Positive control group | 100 mg | 10 | 8.20 ± 2.19 | 3.55 ± 1.21** | 6.20 ± 1.82▲ |
| Test drug low-dose group | 2.0 | 10 | 8.22 ± 1.54 | 3.48 ± 1.36** | 5.15 ± 1.62 |
| Test drug medium-dose group | 4.0 | 10 | 8.32 ± 1.73 | 3.50 ± 1.02** | 6.40 ± 1.92▲ |
| Test drug high-dose group | 12.0 | 10 | 8.42 ± 1.89 | 3.29 ± 1.13** | 6.92 ± 1.87▲▲ |

*P < 0.05,

**P < 0.01 vs. normal control group;

▲P < 0.05,

▲▲P < 0.01 vs. model control group.

TABLE 2

Effect of Composition 1 on the contents of bone marrow BCM and DNA in mice injected with cyclophosphamide ($\bar{x} \pm s$)

| Groups | Dose (g crude drug/kg) | Number of animals | Bone marrow BCM ($\times 10^6$) | Bone marrow DNA |
|---|---|---|---|---|
| Normal control group | 0.0 | 10 | 16.01 ± 2.42 | 0.913 ± 0.276 |
| Model control group | 0.0 | 10 | 10.9 ± 2.63** | 0.422 ± 0.108** |
| Positive control group | 100 mg | 10 | 13.44 ± 2.36▲ | 0.610 ± 0.138▲▲ |
| Test drug low-dose group | 2.0 | 10 | 12.18 ± 1.97 | 0.523 ± 0.142 |

TABLE 2-continued

Effect of Composition 1 on the contents of bone marrow BCM and DNA in mice injected with cyclophosphamide ($\bar{x} \pm s$)

| Groups | Dose (g crude drug/kg) | Number of animals | Bone marrow BCM (×10$^6$) | Bone marrow DNA |
|---|---|---|---|---|
| Test drug medium-dose group | 4.0 | 10 | 13.56 ± 2.78▲ | 0.602 ± 0.157▲ |
| Test drug high-dose group | 12.0 | 10 | 14.49 ± 2.95▲▲ | 0.680 ± 0.176▲▲ |

*P < 0.05,
**P < 0.01 vs. normal control group;
▲P < 0.05,
▲▲P < 0.01 vs. model control group.

3.2 Effect of Composition 1 on Leucocyte Reduction in Mice Induced by Cytarabine Test results are shown in Tables 3 and 4. The number of peripheral WBC and the contents of bone marrow nucleated cells and DNA in the model control group decreased as compared to those in the normal control group, suggesting a successful modeling. Compared to the model control group, the number of peripheral WBC and the contents of bone marrow nucleated cells and DNA significantly increased in the Composition 1 high- and medium-dose groups and in the positive control group, and also showed a tendency to increase in the Composition 1 low-dose group, indicating that Composition 1 can resist leucocyte induction in mice induced by cytarabine and improve the hematopoietic function of the bone marrow thereof.

3.3 Effect of Composition 1 on Leucocyte Reduction in Mice Induced by X-Ray Radiation Test results are shown in Tables 5 and 6. The number of peripheral WBC and the contents of bone marrow nucleated cells and DNA in the model control group decreased as compared to those in the normal control group, suggesting a successful modeling. Compared to the model control group, the number of peripheral WBC and the contents of bone marrow nucleated cells and DNA significantly increased in the Composition 1 high- and medium-dose groups and in the positive control group, and also showed a tendency to increase in the Composition 1 low-dose group, indicating that Composition 1 can resist leucocyte induction in mice induced by X-ray radiation and improve the hematopoietic function of the bone marrow thereof.

TABLE 3

Effect of Composition 1 on peripheral leucocyte reduction in mice induced by cytarabine ($\bar{x} \pm s$, ×10$^9$)

| Groups | Dose (g crude drug/kg) | Number of animals | WBC before modeling | WBC after modeling | WBC after treatment |
|---|---|---|---|---|---|
| Normal control group | 0.0 | 10 | 8.45 ± 1.87 | 8.59 ± 1.90 | 8.74 ± 2.13 |
| Model control group | 0.0 | 10 | 8.62 ± 1.92 | 3.67 ± 1.20** | 4.47 ± 1.26** |
| Positive control group | 100 mg | 10 | 8.50 ± 2.32 | 3.80 ± 1.03** | 6.54 ± 1.93▲▲ |
| Test drug low-dose group | 2.0 | 10 | 8.33 ± 1.69 | 3.54 ± 1.21** | 5.44 ± 1.09 |
| Test drug medium-dose group | 4.0 | 10 | 8.45 ± 1.85 | 3.76 ± 1.09** | 6.07 ± 1.23▲ |
| Test drug high-dose group | 12.0 | 10 | 8.29 ± 2.08 | 3.48 ± 1.03** | 6.87 ± 1.50▲▲ |

*P < 0.05,
**P < 0.01 vs. normal control group;
▲P < 0.05,
▲▲P < 0.01 vs. model control group.

TABLE 4

Effect of Composition 1 on the contents of bone marrow BCM and DNA in mice injected with cytarabine ($\bar{x} \pm s$)

| Groups | Dose (g crude drug/kg) | Number of animals | Bone marrow BCM (×10$^6$) | Bone marrow DNA |
|---|---|---|---|---|
| Normal control group | 0.0 | 10 | 15.38 ± 2.60 | 0.945 ± 0.292 |
| Model control group | 0.0 | 10 | 9.86 ± 2.17** | 0.460 ± 0.127** |
| Positive control group | 100 mg | 10 | 12.53 ± 2.24▲ | 0.634 ± 0.130▲▲ |
| Test drug low-dose group | 2.0 | 10 | 11.36 ± 1.85 | 0.544 ± 0.153 |
| Test drug medium-dose group | 4.0 | 10 | 12.49 ± 2.52▲ | 0.627 ± 0.136▲ |
| Test drug high-dose group | 12.0 | 10 | 13.26 ± 2.88▲▲ | 0.709 ± 0.190▲▲ |

*P < 0.05,
**P < 0.01 vs. normal control group;
▲P < 0.05,
▲▲P < 0.01 vs. model control group.

TABLE 5

Effect of Composition 1 on peripheral leucocyte reduction in mice induced by X-ray radiation ($\bar{x} \pm s$, $\times 10^9$)

| Groups | Dose (g crude drug/kg) | Number of animals | WBC before modeling | WBC on day 8 after treatment | WBC on day 15 after treatment |
|---|---|---|---|---|---|
| Normal control group | 0.0 | 10 | 8.92 ± 2.05 | 9.05 ± 2.54 | 9.12 ± 2.30 |
| Model control group | 0.0 | 10 | 8.85 ± 1.80 | 3.89 ± 1.14** | 5.08 ± 1.60** |
| Positive control group | 100 mg | 10 | 8.74 ± 2.21 | 3.66 ± 1.05** | 6.92 ± 1.98▲▲ |
| Test drug low-dose group | 2.0 | 10 | 8.90 ± 1.94 | 3.82 ± 1.12** | 5.75 ± 1.44 |
| Test drug medium-dose group | 4.0 | 10 | 8.68 ± 1.80 | 3.91 ± 1.30** | 6.73 ± 1.29▲ |
| Test drug high-dose group | 12.0 | 10 | 8.79 ± 1.78 | 3.76 ± 1.22** | 7.47 ± 1.41▲▲ |

*$P < 0.05$,
**$P < 0.01$ vs. normal control group;
▲$P < 0.05$,
▲▲$P < 0.01$ vs. model control group.

TABLE 6

Effect of Composition 1 on the contents of bone marrow BCM and DNA in mice after X-ray radiation ($\bar{x} \pm s$)

| Groups | Dose (g crude drug/kg) | Number of animals | Bone marrow BCM ($\times 10^6$) | Bone marrow DNA |
|---|---|---|---|---|
| Normal control group | 0.0 | 10 | 15.85 ± 2.60 | 0.978 ± 0.285 |
| Model control group | 0.0 | 10 | 10.42 ± 2.31** | 0.480 ± 0.124** |
| Positive control group | 100 mg | 10 | 13.20 ± 2.02▲ | 0.637 ± 0.150▲ |
| Test drug low-dose group | 2.0 | 10 | 11.94 ± 1.67 | 0.563 ± 0.121 |
| Test drug medium-dose group | 4.0 | 10 | 13.08 ± 2.62▲▲ | 0.653 ± 0.140▲ |
| Test drug high-dose group | 12.0 | 10 | 14.15 ± 2.76▲▲ | 0.701 ± 0.192▲▲ |

*$P < 0.05$,
**$P < 0.01$ vs. normal control group;
▲$P < 0.05$,
▲▲$P < 0.01$ vs. model control group.

4. Conclusion

The animal experiments demonstrate that Composition 1 obtained in Example 1 can resist leucocyte reduction in mice induced by cyclophosphamide, cytarabine and X-ray radiation and can improve the hematopoietic function of the bone marrow thereof, indicating that Composition 1 may be effective in preventing and treating leucopenia induced by radiotherapy and chemotherapy.

Example 52. Animal Experiment Report of Composition 2 Obtained in Example 2 in Prevention and Treatment of Leucopenia Induced by Radiotherapy or Chemotherapy 1. Materials and Methods
1.1 Sources of Samples The test drug was Composition 2 (Radix Panacis Quinquefolii, *Ganoderma*, and fermented *Cordyceps sinensis* powder) provided by Jiangzhong Pharmaceutical Co. Ltd. as composite powder. 1 g dry composite powder was equivalent to 11.41 g total crude drugs.

1.2 Laboratory Animals
The same as in Example 51.
1.3 Primary Reagents
The same as in Example 51.
1.4 Primary Instruments
The same as in Example 51.
2. Experimental Methods
2.1 Effect of Composition 2 on Leucocyte Reduction in Mice Induced by Cyclophosphamide[1]

2.1.1 Grouping, Modeling and Dosage Regime

Mice were randomly divided into 6 groups with 10 animals per group, i.e., normal control group, model control group, positive control group, and groups on low, medium and high doses of Composition 2. The low-, medium- and high-dose groups were intragastrically given Composition 2 at a dose of 2.0 g crude drug/kg, 4.0 g crude drug/kg, and 12.0 g crude drug/kg, respectively; the positive control group was intragastrically given batyl alcohol (100 mg/kg) at a dose of 0.1 ml/10 g body weight; the normal control group and the model control group were intragastrically given an equivalent volume of distilled water; and the dosage regime lasted for 15 days with one dose per day. From day 9 of intragastrical administration, all mice in each group, except the normal control group, were given cyclophosphamide at a dose of 40 mg/kg each day via subcutaneous injection for 3 consecutive days. One hour after the intragastrical administration on day 15, blood and femurs were harvested for tests.

2.1.2 Peripheral Leucocyte Assay
The same as in Example 51.
2.1.3 Bone Marrow Nucleated Cell Count (BMC)
The same as in Example 51.
2.1.4 Bone Marrow DNA Content Determination
The same as in Example 51.
2.2 Effect of Composition 2 on Leucocyte Reduction in Mice Induced by Cytarabine[2]
2.2.1 Grouping, Modeling and Dosage Regime
The same as in Example 51.
2.2.2 Peripheral Leucocyte Assay, Bone Marrow Nucleated Cell Count, and Bone Marrow DNA Content Determination The same as in 2.1.
2.3 Effect of Composition 2 on Leucocyte Reduction in Mice Induced by X-Ray Radiation[3]
2.3.1 Grouping, Modeling and Dosage Regime
The same as in Example 51.
2.3.2 Peripheral Leucocyte Assay, Bone Marrow Nucleated Cell Count, and Bone Marrow DNA Content Determination
The same as in 2.1.
2.4 Statistic Method
The same as in Example 51.
3. Results
3.1 Effect of Composition 2 on Leucocyte Reduction in Mice Induced by Cyclophosphamide
Test results are shown in Tables 1 and 2. The number of peripheral WBC and the contents of bone marrow nucleated cells and DNA in the model control group decreased as compared to those in the normal control group, suggesting a successful modeling. Compared to the model control group, the number of peripheral WBC and the contents of bone marrow nucleated cells and DNA significantly increased in the Composition 2 high- and medium-dose groups and in the positive control group, and also showed a tendency to increase in the Composition 2 low-dose group, indicating that Composition 2 can resist leucocyte reduction in mice induced by cyclophosphamide and improve the hematopoietic function of the bone marrow thereof.

TABLE 1

Effect of Composition 2 on peripheral leucocyte reduction in mice induced by cyclophosphamide ($\bar{x} \pm s$, $\times 10^9$)

| Groups | Dose (g crude drug/kg) | Number of animals | WBC before modeling | WBC after modeling | WBC after treatment |
|---|---|---|---|---|---|
| Normal control group | 0.0 | 10 | 9.21 ± 1.75 | 9.44 ± 1.72 | 9.35 ± 1.94 |
| Model control group | 0.0 | 10 | 9.33 ± 2.30 | 4.75 ± 1.22** | 5.26 ± 1.72** |
| Positive control group | 100 mg | 10 | 9.42 ± 2.12 | 4.64 ± 1.30** | 7.34 ± 1.59▲▲ |
| Test drug low-dose group | 2.0 | 10 | 9.20 ± 1.89 | 4.60 ± 1.41** | 6.24 ± 1.88 |
| Test drug medium-dose group | 4.0 | 10 | 9.26 ± 1.96 | 4.55 ± 1.25** | 7.21 ± 1.62▲ |
| Test drug high-dose group | 12.0 | 10 | 9.06 ± 1.64 | 4.39 ± 1.32** | 7.81 ± 1.90▲▲ |

*$P < 0.05$,

**$P < 0.01$ vs. normal control group;

▲$P < 0.05$,

▲▲$P < 0.01$ vs. model control group.

TABLE 2

Effect of Composition 2 on the contents of bone marrow BCM and DNA in mice injected with cyclophosphamide ($\bar{x} \pm s$)

| Groups | Dose (g crude drug/kg) | Number of animals | Bone marrow BCM ($\times 10^6$) | Bone marrow DNA |
|---|---|---|---|---|
| Normal control group | 0.0 | 10 | 14.39 ± 2.46 | 0.928 ± 0.264 |
| Model control group | 0.0 | 10 | 9.60 ± 2.72** | 0.440 ± 0.125** |
| Positive control group | 100 mg | 10 | 11.87 ± 2.08▲▲ | 0.629 ± 0.150▲▲ |
| Test drug low-dose group | 2.0 | 10 | 10.95 ± 2.14 | 0.537 ± 0.132 |
| Test drug medium-dose group | 4.0 | 10 | 12.62 ± 2.45▲ | 0.624 ± 0.166▲ |
| Test drug high-dose group | 12.0 | 10 | 13.42 ± 2.80▲▲ | 0.699 ± 0.169▲▲ |

*$P < 0.05$,

**$P < 0.01$ vs. normal control group;

▲$P < 0.05$,

▲▲$P < 0.01$ vs. model control group.

3.2 Effect of Composition 2 on Leucocyte Reduction in Mice Induced by Cytarabine Test results are shown in Tables 3 and 4. The number of peripheral WBC and the contents of bone marrow nucleated cells and DNA in the model control group decreased as compared to those in the normal control group, suggesting a successful modeling. Compared to the model control group, the number of peripheral WBC and the contents of bone marrow nucleated cells and DNA significantly increased in the Composition 2 high- and medium-dose groups and in the positive control group, and also showed a tendency to increase in the Composition 2 low-dose group, indicating that Composition 2 can resist leucocyte induction in mice induced by cytarabine and improve the hematopoietic function of the bone marrow thereof.

TABLE 3

Effect of Composition 2 on peripheral leucocyte reduction in mice induced by cytarabine ($\bar{x} \pm s$, $\times 10^9$)

| Groups | Dose (g crude drug/kg) | Number of animals | WBC before modeling | WBC after modeling | WBC after treatment |
|---|---|---|---|---|---|
| Normal control group | 0.0 | 10 | 8.70 ± 1.76 | 8.90 ± 1.44 | 8.94 ± 2.20 |
| Model control group | 0.0 | 10 | 8.92 ± 1.88 | 4.58 ± 1.36** | 4.70 ± 1.16** |
| Positive control group | 100 mg | 10 | 8.68 ± 2.03 | 4.67 ± 1.27** | 6.85 ± 1.70▲▲ |
| Test drug low-dose group | 2.0 | 10 | 8.78 ± 1.96 | 4.80 ± 1.08** | 5.73 ± 1.23 |
| Test drug medium-dose group | 4.0 | 10 | 8.85 ± 2.13 | 4.38 ± 1.14** | 6.17 ± 1.23▲ |
| Test drug high-dose group | 12.0 | 10 | 8.69 ± 2.01 | 4.62 ± 1.18** | 7.38 ± 2.44▲▲ |

*$P < 0.05$,

**$P < 0.01$ vs. normal control group;

▲$P < 0.05$,

▲▲$P < 0.01$ vs. model control group.

TABLE 4

Effect of Composition 2 on the contents of bone marrow BCM and DNA in mice injected with cytarabine ($\bar{x} \pm s$)

| Groups | Dose (g crude drug/kg) | Number of animals | Bone marrow BCM ($\times 10^6$) | Bone marrow DNA |
|---|---|---|---|---|
| Normal control group | 0.0 | 10 | 15.92 ± 2.60 | 0.993 ± 0.267 |
| Model control group | 0.0 | 10 | 10.61 ± 2.82** | 0.503 ± 0.161** |
| Positive control group | 100 mg | 10 | 13.95 ± 2.77▲ | 0.684 ± 0.152▲ |
| Test drug low-dose group | 2.0 | 10 | 11.90 ± 2.20 | 0.590 ± 0.142 |
| Test drug medium-dose group | 4.0 | 10 | 13.44 ± 2.70▲ | 0.676 ± 0.128▲ |
| Test drug high-dose group | 12.0 | 10 | 14.08 ± 1.92▲▲ | 0.733 ± 0.181▲▲ |

*$P < 0.05$,

**$P < 0.01$ vs. normal control group;

▲$P < 0.05$,

▲▲$P < 0.01$ vs. model control group.

3.3 Effect of Composition 2 on Leucocyte Reduction in Mice Induced by X-Ray Radiation Test results are shown in Tables 5 and 6. The number of peripheral WBC and the contents of bone marrow nucleated cells and DNA in the model control group decreased as compared to those in the normal control group, suggesting a successful modeling. Compared to the model control group, the number of peripheral WBC and the contents of bone marrow nucleated cells and DNA significantly increased in the Composition 2 high- and medium-dose groups and in the positive control group, and also showed a tendency to increase in the Composition 2 low-dose group, indicating that Composition 2 can resist leucocyte induction in mice induced by X-ray radiation and improve the hematopoietic function of the bone marrow thereof.

TABLE 5

Effect of Composition 2 on peripheral leucocyte reduction in mice induced by X-ray radiation ($\bar{x} \pm s$, $\times 10^9$)

| Groups | Dose (g crude drug/kg) | Number of animals | WBC before modeling | WBC on day 8 after treatment | WBC on day 15 after treatment |
|---|---|---|---|---|---|
| Normal control group | 0.0 | 10 | 10.24 ± 2.05 | 10.02 ± 2.32 | 10.12 ± 2.41 |
| Model control group | 0.0 | 10 | 10.47 ± 2.14 | 5.38 ± 1.33** | 5.16 ± 1.44** |
| Positive control group | 100 mg | 10 | 10.16 ± 2.30 | 5.60 ± 1.28** | 7.04 ± 1.87▲ |
| Test drug low-dose group | 2.0 | 10 | 10.58 ± 1.89 | 5.52 ± 1.19** | 6.28 ± 1.50 |
| Test drug medium-dose group | 4.0 | 10 | 10.32 ± 1.62 | 5.24 ± 1.21** | 6.94 ± 1.66▲ |
| Test drug high-dose group | 12.0 | 10 | 10.27 ± 1.33 | 5.46 ± 1.20** | 7.26 ± 1.48▲▲ |

*$p < 0.05$,
**$p < 0.01$ vs. normal control group;
▲$p < 0.05$,
▲▲$p < 0.01$ vs. model control group.

TABLE 6

Effect of Composition 2 on the contents of bone marrow BCM and DNA in mice after X-ray radiation ($\bar{x} \pm s$)

| Groups | Dose (g crude drug/kg) | Number of animals | Bone marrow BCM ($\times 10^6$) | Bone marrow DNA |
|---|---|---|---|---|
| Normal control group | 0.0 | 10 | 14.32 ± 2.78 | 0.916 ± 0.274 |
| Model control group | 0.0 | 10 | 9.15 ± 2.07** | 0.425 ± 0.108** |
| Positive control group | 100 mg | 10 | 12.43 ± 2.29▲ | 0.589 ± 0.123▲▲ |
| Test drug low-dose group | 2.0 | 10 | 11.03 ± 1.90 | 0.514 ± 0.119 |
| Test drug medium-dose group | 4.0 | 10 | 12.20 ± 2.82▲▲ | 0.609 ± 0.126▲▲ |
| Test drug high-dose group | 12.0 | 10 | 13.09 ± 2.55▲▲ | 0.685 ± 0.187▲▲ |

*$p < 0.05$,
**$p < 0.01$ vs. normal control group;
▲$p < 0.05$,
▲▲$p < 0.01$ vs. model control group.

4. Conclusion

The animal experiments demonstrate that Composition 2 obtained in Example 2 can resist leucocyte reduction in mice induced by cyclophosphamide, cytarabine and X-ray radiation and can improve the hematopoietic function of the bone marrow thereof, indicating that Composition 2 may be effective in preventing and treating leucopenia induced by radiotherapy and chemotherapy.

Example 53. Animal Experiment Report of Composition 3 Obtained in Example 3 in Prevention and Treatment of Leucopenia Induced by Radiotherapy or Chemotherapy 1. Materials and Methods 1.1 Sources of Samples The test drug was Composition 3 (Radix Panacis Quinquefolii, Ganoderma, fermented Cordyceps sinensis powder and Cordyceps) provided by Jiangzhong Pharmaceutical Co. Ltd. as composite powder. 1 g dry composite powder was equivalent to 12.39 g total crude drugs.

1.2 Laboratory Animals

The same as in Example 51.

1.3 Primary Reagents

The same as in Example 51.

1.4 Primary Instruments

The same as in Example 51.

2. Experimental Methods 2.1 Effect of Composition 3 on Leucocyte Reduction in Mice Induced by Cyclophosphamide[1]

2.1.1 Grouping, Modeling and Dosage Regime

Mice were randomly divided into 6 groups with 10 animals per group, i.e., normal control group, model control group, positive control group, and groups on low, medium and high doses of Composition 3. The low-, medium- and high-dose groups were intragastrically given Composition 3 at a dose of 2.0 g crude drug/kg, 4.0 g crude drug/kg, and 12.0 g crude drug/kg, respectively; the positive control group was intragastrically given batyl alcohol (100 mg/kg) at a dose of 0.1 ml/10 g body weight; the normal control group and the model control group were intragastrically given an equivalent volume of distilled water; and the dosage regime lasted for 15 days with one dose per day. From day 9 of intragastrical administration, all mice in each group, except the normal control group, were given cyclophosphamide at a dose of 40 mg/kg each day via subcutaneous injection for 3 consecutive days. One hour after the intragastrical administration on day 15, blood and femurs were harvested for tests.

2.1.2 Peripheral Leucocyte Assay
The same as in Example 51.
2.1.3 Bone Marrow Nucleated Cell Count (BMC)
The same as in Example 51.
2.1.4 Bone Marrow DNA Content Determination
The same as in Example 51.
2.2 Effect of Composition 3 on Leucocyte Reduction in Mice Induced by Cytarabine[2]
2.2.1 Grouping, Modeling and Dosage Regime
The same as in Example 51.
2.2.2 Peripheral Leucocyte Assay, Bone Marrow Nucleated Cell Count, and Bone Marrow DNA Content Determination
The same as in 2.1.
2.3 Effect of Composition 3 on Leucocyte Reduction in Mice Induced by X-Ray Radiation[3]
2.3.1 Grouping, Modeling and Dosage Regime
The same as in Example 51.
2.3.2 Peripheral Leucocyte Assay, Bone Marrow Nucleated Cell Count, and Bone Marrow DNA Content Determination
The same as in 2.1.
2.4 Statistic Method
The same as in Example 51.
3. Results
3.1 Effect of Composition 3 on Leucocyte Reduction in Mice Induced by Cyclophosphamide Test results are shown in Tables 1 and 2. The number of peripheral WBC and the contents of bone marrow nucleated cells and DNA in the model control group decreased as compared to those in the normal control group, suggesting a successful modeling. Compared to the model control group, the number of peripheral WBC and the contents of bone marrow nucleated cells and DNA significantly increased in the Composition 3 high- and medium-dose groups and in the positive control group, and also showed a tendency to increase in the Composition 3 low-dose group, indicating that Composition 3 can resist leucocyte reduction in mice induced by cyclophosphamide and improve the hematopoietic function of the bone marrow thereof.

TABLE 1

Effect of Composition 3 on peripheral leucocyte reduction in mice induced by cyclophosphamide ($\bar{x} \pm s$, $\times 10^9$)

| Groups | Dose (g crude drug/kg) | Number of animals | WBC before modeling | WBC after modeling | WBC after treatment |
|---|---|---|---|---|---|
| Normal control group | 0.0 | 10 | 9.55 ± 1.90 | 9.82 ± 2.04 | 9.69 ± 1.77 |
| Model control group | 0.0 | 10 | 9.70 ± 2.04 | 5.03 ± 1.28** | 5.20 ± 1.76** |
| Positive control group | 100 mg | 10 | 9.27 ± 2.21 | 5.25 ± 1.30** | 7.56 ± 1.80▲▲ |
| Test drug low-dose group | 2.0 | 10 | 9.80 ± 1.96 | 5.18 ± 1.41** | 6.50 ± 1.62 |
| Test drug medium-dose group | 4.0 | 10 | 9.64 ± 1.88 | 5.23 ± 1.25** | 7.24 ± 1.88▲ |
| Test drug high-dose group | 12.0 | 10 | 9.55 ± 1.79 | 5.40 ± 1.32** | 7.94 ± 1.94▲▲ |

*$P < 0.05$,

**$P < 0.01$ vs. normal control group;

▲$P < 0.05$,

▲▲$P < 0.01$ vs. model control group.

TABLE 2

Effect of Composition 3 on the contents of bone marrow BCM and DNA in mice injected with cyclophosphamide ($\bar{x} \pm s$)

| Groups | Dose (g crude drug/kg) | Number of animals | Bone marrow BCM ($\times 10^6$) | Bone marrow DNA |
|---|---|---|---|---|
| Normal control group | 0.0 | 10 | 15.42 ± 2.86 | 0.877 ± 0.212 |
| Model control group | 0.0 | 10 | 10.88 ± 2.13** | 0.438 ± 0.107** |
| Positive control group | 100 mg | 10 | 13.65 ± 2.42▲ | 0.625 ± 0.162▲▲ |
| Test drug low-dose group | 2.0 | 10 | 12.80 ± 2.33 | 0.584 ± 0.140 |
| Test drug medium-dose group | 4.0 | 10 | 13.23 ± 2.72▲ | 0.635 ± 0.172▲▲ |
| Test drug high-dose group | 12.0 | 10 | 13.99 ± 1.93▲▲ | 0.684 ± 0.155▲▲ |

*$P < 0.05$,

**$P < 0.01$ vs. normal control group;

▲$P < 0.05$,

▲▲$P < 0.01$ vs. model control group.

3.2 Effect of Composition 3 on Leucocyte Reduction in Mice Induced by Cytarabine Test results are shown in Tables 3 and 4. The number of peripheral WBC and the contents of bone marrow nucleated cells and DNA in the model control group decreased as compared to those in the normal control group, suggesting a successful modeling. Compared to the model control group, the number of peripheral WBC and the contents of bone marrow nucleated cells and DNA significantly increased in the Composition 3 high- and medium-dose groups and in the positive control group, and also showed a tendency to increase in the Composition 3 low-dose group, indicating that Composition 3 can resist leucocyte induction in mice induced by cytarabine and improve the hematopoietic function of the bone marrow thereof.

TABLE 3

Effect of Composition 3 on peripheral leucocyte reduction in mice induced by cytarabine ($\bar{x} \pm s$, $\times 10^9$)

| Groups | Dose (g crude drug/kg) | Number of animals | WBC before modeling | WBC after modeling | WBC after treatment |
| --- | --- | --- | --- | --- | --- |
| Normal control group | 0.0 | 10 | 9.22 ± 1.80 | 9.30 ± 1.86 | 9.51 ± 2.26 |
| Model control group | 0.0 | 10 | 9.45 ± 1.92 | 4.83 ± 1.51** | 4.73 ± 1.34** |
| Positive control group | 100 mg | 10 | 9.30 ± 2.14 | 4.90 ± 1.43** | 7.10 ± 1.88▲▲ |
| Test drug low-dose group | 2.0 | 10 | 9.26 ± 1.54 | 4.84 ± 1.26** | 5.66 ± 1.45 |
| Test drug medium-dose group | 4.0 | 10 | 9.17 ± 2.07 | 4.64 ± 1.33** | 6.52 ± 1.48▲ |
| Test drug high-dose group | 12.0 | 10 | 9.23 ± 2.21 | 4.91 ± 1.27** | 7.29 ± 1.90▲▲ |

*$P < 0.05$,

**$P < 0.01$ vs. normal control group;

▲$P < 0.05$,

▲▲$P < 0.01$ vs. model control group.

TABLE 4

Effect of Composition 3 on the contents of bone marrow BCM and DNA in mice injected with cytarabine ($\bar{x} \pm s$)

| Groups | Dose (g crude drug/kg) | Number of animals | Bone marrow BCM ($\times 10^6$) | Bone marrow DNA |
| --- | --- | --- | --- | --- |
| Normal control group | 0.0 | 10 | 15.60 ± 2.72 | 0.980 ± 0.209 |
| Model control group | 0.0 | 10 | 10.37 ± 2.43** | 0.524 ± 0.142** |
| Positive control group | 100 mg | 10 | 13.64 ± 2.19▲ | 0.713 ± 0.138▲▲ |
| Test drug low-dose group | 2.0 | 10 | 11.53 ± 2.34 | 0.621 ± 0.151 |
| Test drug medium-dose group | 4.0 | 10 | 13.10 ± 2.56▲ | 0.693 ± 0.136▲ |
| Test drug high-dose group | 12.0 | 10 | 14.21 ± 2.80▲▲ | 0.748 ± 0.175▲▲ |

*$P < 0.05$,

**$P < 0.01$ vs. normal control group;

▲$P < 0.05$,

▲▲$P < 0.01$ vs. model control group.

3.3 Effect of Composition 3 on Leucocyte Reduction in Mice Induced by X-Ray Radiation Test results are shown in Tables 5 and 6. The number of peripheral WBC and the contents of bone marrow nucleated cells and DNA in the model control group decreased as compared to those in the normal control group, suggesting a successful modeling. Compared to the model control group, the number of peripheral WBC and the contents of bone marrow nucleated cells and DNA significantly increased in the Composition 3 high- and medium-dose groups and in the positive control group, and also showed a tendency to increase in the Composition 3 low-dose group, indicating that Composition 3 can resist leucocyte induction in mice induced by X-ray radiation and improve the hematopoietic function of the bone marrow thereof.

TABLE 5

Effect of Composition 3 on peripheral leucocyte reduction in mice induced by X-ray radiation ($\bar{x} \pm s$, $\times 10^9$)

| Groups | Dose (g crude drug/kg) | Number of animals | WBC before modeling | WBC on day 8 after treatment | WBC on day 15 after treatment |
| --- | --- | --- | --- | --- | --- |
| Normal control group | 0.0 | 10 | 10.54 ± 2.18 | 10.16 ± 2.05 | 10.43 ± 2.35 |
| Model control group | 0.0 | 10 | 10.60 ± 2.09 | 5.92 ± 1.38** | 5.88 ± 1.70** |
| Positive control group | 100 mg | 10 | 10.88 ± 2.24 | 5.87 ± 1.62** | 7.49 ± 1.52▲ |
| Test drug low-dose group | 2.0 | 10 | 10.27 ± 1.92 | 5.65 ± 1.40** | 6.89 ± 1.33 |
| Test drug medium-dose group | 4.0 | 10 | 10.58 ± 2.30 | 5.80 ± 1.53** | 7.61 ± 1.53▲ |
| Test drug high-dose group | 12.0 | 10 | 10.37 ± 2.33 | 5.74 ± 1.38** | 8.22 ± 1.60▲▲ |

*$P < 0.05$,
**$P < 0.01$ vs. normal control group;
▲$P < 0.05$,
▲▲$P < 0.01$ vs. model control group.

TABLE 6

Effect of Composition 3 on the contents of bone marrow BCM and DNA in mice after X-ray radiation ($\bar{x} \pm s$)

| Groups | Dose (g crude drug/kg) | Number of animals | Bone marrow BCM ($\times 10^6$) | Bone marrow DNA |
| --- | --- | --- | --- | --- |
| Normal control group | 0.0 | 10 | 16.50 ± 2.80 | 0.998 ± 0.258 |
| Model control group | 0.0 | 10 | 11.27 ± 2.34** | 0.520 ± 0.120** |
| Positive control group | 100 mg | 10 | 13.69 ± 2.65▲ | 0.723 ± 0.135▲▲ |
| Test drug low-dose group | 2.0 | 10 | 13.22 ± 2.18 | 0.626 ± 0.127 |
| Test drug medium-dose group | 4.0 | 10 | 14.40 ± 2.43▲▲ | 0.734 ± 0.178▲▲ |
| Test drug high-dose group | 12.0 | 10 | 15.17 ± 2.26▲▲ | 0.765 ± 0.166▲▲ |

*$P < 0.05$,
**$P < 0.01$ vs. normal control group;
▲$P < 0.05$,
▲▲$P < 0.01$ vs. model control group.

4. Conclusion

The animal experiments demonstrate that Composition 3 obtained in Example 3 can resist leucocyte reduction in mice induced by cyclophosphamide, cytarabine and X-ray radiation and can improve the hematopoietic function of the bone marrow thereof, indicating that Composition 3 may be effective in preventing and treating leucopenia induced by radiotherapy and chemotherapy.

Example 54. Animal Experiment Report of Composition 4 Obtained in Example 4 in Prevention and Treatment of Leucopenia Induced by Radiotherapy or Chemotherapy 1. Materials and Methods 1.1 Sources of Samples The test drug was Composition 4 (Radix Panacis Quinquefolii, Ganoderma, Cordyceps, and Flos Rosae Rugosae) provided by Jiangzhong Pharmaceutical Co. Ltd. as composite powder. 1 g dry composite powder was equivalent to 12.19 g total crude drugs.

1.2 Laboratory Animals

The same as in Example 51.

1.3 Primary Reagents

The same as in Example 51.

1.4 Primary Instruments

The same as in Example 51.

2. Experimental Methods 2.1 Effect of Composition 4 on Leucocyte Reduction in Mice Induced by Cyclophosphamide[1]

2.1.1 Grouping, Modeling and Dosage Regime

Mice were randomly divided into 6 groups with 10 animals per group, i.e., normal control group, model control group, positive control group, and groups on low, medium and high doses of Composition 4. The low-, medium- and high-dose groups were intragastrically given Composition 4 at a dose of 2.0 g crude drug/kg, 4.0 g crude drug/kg, and 12.0 g crude drug/kg, respectively; the positive control group was intragastrically given batyl alcohol (100 mg/kg) at a dose of 0.1 ml/10 g body weight; the normal control group and the model control group were intragastrically given an equivalent volume of distilled water; and the dosage regime lasted for 15 days with one dose per day. From day 9 of intragastrical administration, all mice in each group, except the normal control group, were given cyclophosphamide at a dose of 40 mg/kg each day via subcutaneous injection for 3 consecutive days. One hour after the intragastrical administration on day 15, blood and femurs were harvested for tests.

2.1.2 Peripheral Leucocyte Assay
The same as in Example 51.

2.1.3 Bone Marrow Nucleated Cell Count (BMC)
The same as in Example 51.

2.1.4 Bone Marrow DNA Content Determination
The same as in Example 51.

2.2 Effect of Composition 4 on Leucocyte Reduction in Mice Induced by Cytarabine[2]

2.2.1 Grouping, Modeling and Dosage Regime
The same as in Example 51.

2.2.2 Peripheral Leucocyte Assay, Bone Marrow Nucleated Cell Count, and Bone Marrow DNA Content Determination
The same as in 2.1.

2.3 Effect of Composition 4 on Leucocyte Reduction in Mice Induced by X-Ray Radiation[3]

2.3.1 Grouping, Modeling and Dosage Regime
The same as in Example 51.

2.3.2 Peripheral Leucocyte Assay, Bone Marrow Nucleated Cell Count, and Bone Marrow DNA Content Determination
The same as in 2.1.

2.4 Statistic Method
The same as in Example 51.

3. Results 3.1 Effect of Composition 4 on Leucocyte Reduction in Mice Induced by Cyclophosphamide Test results are shown in Tables 1 and 2. The number of peripheral WBC and the contents of bone marrow nucleated cells and DNA in the model control group decreased as compared to those in the normal control group, suggesting a successful modeling. Compared to the model control group, the number of peripheral WBC and the contents of bone marrow nucleated cells and DNA significantly increased in the Composition 4 high- and medium-dose groups and in the positive control group, and also showed a tendency to increase in the Composition 4 low-dose group, indicating that Composition 4 can resist leucocyte reduction in mice induced by cyclophosphamide and improve the hematopoietic function of the bone marrow thereof.

TABLE 1

Effect of Composition 4 on peripheral leucocyte reduction in mice induced by cyclophosphamide ($\bar{x} \pm s$, $\times 10^9$)

| Groups | Dose (g crude drug/kg) | Number of animals | WBC before modeling | WBC after modeling | WBC after treatment |
|---|---|---|---|---|---|
| Normal control group | 0.0 | 10 | 10.43 ± 1.88 | 10.81 ± 2.61 | 10.60 ± 2.32 |
| Model control group | 0.0 | 10 | 10.56 ± 2.14 | 5.77 ± 1.62** | 5.96 ± 1.78** |
| Positive control group | 100 mg | 10 | 10.29 ± 2.30 | 6.13 ± 1.47** | 8.23 ± 1.54▲▲ |
| Test drug low-dose group | 2.0 | 10 | 10.74 ± 2.11 | 5.86 ± 1.38** | 7.48 ± 1.86 |
| Test drug medium-dose group | 4.0 | 10 | 10.27 ± 2.26 | 6.08 ± 1.62** | 8.10 ± 2.03▲ |
| Test drug high-dose group | 12.0 | 10 | 10.50 ± 2.09 | 5.94 ± 1.55** | 8.52 ± 1.90▲▲ |

*$P < 0.05$,
**$P < 0.01$ vs. normal control group;
▲$P < 0.05$,
▲▲$P < 0.01$ vs. model control group.

TABLE 2

Effect of Composition 4 on the contents of bone marrow BCM and DNA in mice injected with cyclophosphamide ($\bar{x} \pm s$)

| Groups | Dose (g crude drug/kg) | Number of animals | Bone marrow BCM ($\times 10^6$) | Bone marrow DNA |
|---|---|---|---|---|
| Normal control group | 0.0 | 10 | 16.60 ± 2.92 | 0.956 ± 0.233 |
| Model control group | 0.0 | 10 | 11.86 ± 2.21** | 0.544 ± 0.132** |
| Positive control group | 100 mg | 10 | 14.73 ± 2.04▲ | 0.730 ± 0.150▲▲ |
| Test drug low-dose group | 2.0 | 10 | 13.93 ± 2.26 | 0.660 ± 0.138 |
| Test drug medium-dose group | 4.0 | 10 | 14.35 ± 2.51▲ | 0.752 ± 0.169▲▲ |
| Test drug high-dose group | 12.0 | 10 | 14.90 ± 1.88▲▲ | 0.786 ± 0.172▲▲ |

*$P < 0.05$,
**$P < 0.01$ vs. normal control group;
▲$P < 0.05$,
▲▲$P < 0.01$ vs. model control group.

3.2 Effect of Composition 4 on Leucocyte Reduction in Mice Induced by Cytarabine Test results are shown in Tables 3 and 4. The number of peripheral WBC and the contents of bone marrow nucleated cells and DNA in the model control group decreased as compared to those in the normal control group, suggesting a successful modeling. Compared to the model control group, the number of peripheral WBC and the contents of bone marrow nucleated cells and DNA significantly increased in the Composition 4 high- and medium-dose groups and in the positive control group, and also showed a tendency to increase in the Composition 4 low-dose group, indicating that Composition 4 can resist leucocyte induction in mice induced by cytarabine and improve the hematopoietic function of the bone marrow thereof.

TABLE 3

Effect of Composition 4 on peripheral leucocyte reduction in mice induced by cytarabine ($\bar{x} \pm s$, $\times 10^9$)

| Groups | Dose (g crude drug/kg) | Number of animals | WBC before modeling | WBC after modeling | WBC after treatment |
|---|---|---|---|---|---|
| Normal control group | 0.0 | 10 | 8.16 ± 1.76 | 8.36 ± 1.58 | 8.47 ± 1.95 |
| Model control group | 0.0 | 10 | 8.50 ± 1.54 | 4.51 ± 1.61** | 4.48 ± 1.58** |
| Positive control group | 100 mg | 10 | 8.28 ± 1.62 | 4.16 ± 1.09** | 7.26 ± 1.90▲▲ |
| Test drug low-dose group | 2.0 | 10 | 8.53 ± 2.08 | 4.66 ± 1.17** | 5.54 ± 1.75 |
| Test drug medium-dose group | 4.0 | 10 | 8.60 ± 2.11 | 4.35 ± 1.25** | 6.71 ± 1.98▲ |
| Test drug high-dose group | 12.0 | 10 | 8.29 ± 1.65 | 4.27 ± 1.41** | 7.16 ± 1.22▲▲ |

*$P < 0.05$,

**$P < 0.01$ vs. normal control group;

▲$P < 0.05$,

▲▲$P < 0.01$ vs. model control group.

TABLE 4

Effect of Composition 4 on the contents of bone marrow BCM and DNA in mice injected with cytarabine ($\bar{x} \pm s$)

| Groups | Dose (g crude drug/kg) | Number of animals | Bone marrow BCM ($\times 10^6$) | Bone marrow DNA |
|---|---|---|---|---|
| Normal control group | 0.0 | 10 | 17.21 ± 2.96 | 1.052 ± 0.226 |
| Model control group | 0.0 | 10 | 11.16 ± 2.88** | 0.673 ± 0.145** |
| Positive control group | 100 mg | 10 | 14.32 ± 2.65▲ | 0.879 ± 0.169▲▲ |
| Test drug low-dose group | 2.0 | 10 | 13.66 ± 2.78 | 0.802 ± 0.184 |
| Test drug medium-dose group | 4.0 | 10 | 14.50 ± 2.90▲ | 0.868 ± 0.166▲ |
| Test drug high-dose group | 12.0 | 10 | 15.63 ± 2.67▲▲ | 0.944 ± 0.190▲▲ |

*$P < 0.05$,

**$P < 0.01$ vs. normal control group;

▲$P < 0.05$,

▲▲$P < 0.01$ vs. model control group.

3.3 Effect of Composition 4 on Leucocyte Reduction in Mice Induced by X-Ray Radiation Test results are shown in Tables 5 and 6. The number of peripheral WBC and the contents of bone marrow nucleated cells and DNA in the model control group decreased as compared to those in the normal control group, suggesting a successful modeling. Compared to the model control group, the number of peripheral WBC and the contents of bone marrow nucleated cells and DNA significantly increased in the Composition 4 high- and medium-dose groups and in the positive control group, and also showed a tendency to increase in the Composition 4 low-dose group, indicating that Composition 4 can resist leucocyte induction in mice induced by X-ray radiation and improve the hematopoietic function of the bone marrow thereof.

TABLE 5

Effect of Composition 4 on peripheral leucocyte reduction in mice induced by X-ray radiation ($\bar{x} \pm s$, $\times 10^9$)

| Groups | Dose (g crude drug/kg) | Number of animals | WBC before modeling | WBC on day 8 after treatment | WBC on day 15 after treatment |
|---|---|---|---|---|---|
| Normal control group | 0.0 | 10 | 9.67 ± 2.26 | 9.33 ± 2.15 | 9.46 ± 2.20 |
| Model control group | 0.0 | 10 | 9.36 ± 2.17 | 5.71 ± 1.20** | 5.60 ± 1.45** |
| Positive control group | 100 mg | 10 | 9.42 ± 2.05 | 5.80 ± 1.44** | 7.88 ± 1.61▲▲ |
| Test drug low-dose group | 2.0 | 10 | 9.57 ± 1.77 | 5.24 ± 1.07** | 6.76 ± 1.22 |
| Test drug medium-dose group | 4.0 | 10 | 9.83 ± 2.08 | 5.33 ± 1.18** | 7.40 ± 1.48▲ |
| Test drug high-dose group | 12.0 | 10 | 9.47 ± 2.19 | 5.52 ± 1.24** | 8.36 ± 1.55▲▲ |

*$P < 0.05$,
**$P < 0.01$ vs. normal control group;
▲$P < 0.05$,
▲▲$P < 0.01$ vs. model control group.

TABLE 6

Effect of Composition 4 on the contents of bone marrow BCM and DNA in mice after X-ray radiation ($\bar{x} \pm s$)

| Groups | Dose (g crude drug/kg) | Number of animals | Bone marrow BCM ($\times 10^6$) | Bone marrow DNA |
|---|---|---|---|---|
| Normal control group | 0.0 | 10 | 17.06 ± 2.96 | 0.972 ± 0.224 |
| Model control group | 0.0 | 10 | 12.11 ± 2.03** | 0.541 ± 0.109** |
| Positive control group | 100 mg | 10 | 14.57 ± 2.57▲ | 0.760 ± 0.147▲▲ |
| Test drug low-dose group | 2.0 | 10 | 14.06 ± 2.42 | 0.644 ± 0.122 |
| Test drug medium-dose group | 4.0 | 10 | 15.31 ± 2.60▲▲ | 0.752 ± 0.103▲▲ |
| Test drug high-dose group | 12.0 | 10 | 16.02 ± 2.33▲▲ | 0.786 ± 0.148▲▲ |

*$P < 0.05$,
**$P < 0.01$ vs. normal control group;
▲$P < 0.05$,
▲▲$P < 0.01$ vs. model control group.

4. Conclusion

The animal experiments demonstrate that Composition 4 obtained in Example 4 can resist leucocyte reduction in mice induced by cyclophosphamide, cytarabine and X-ray radiation and can improve the hematopoietic function of the bone marrow thereof, indicating that Composition 4 may be effective in preventing and treating leucopenia induced by radiotherapy and chemotherapy.

Example 55. Animal Experiment Report of Composition 5 Obtained in Example 5 in Prevention and Treatment of Leucopenia Induced by Radiotherapy or Chemotherapy 1. Materials and Methods
1.1 Sources of Samples The test drug was Composition 5 (Radix Panacis Quinquefolii, *Ganoderma*, fermented *Cordyceps sinensis* powder, and Flos Rosae Rugosae) provided by Jiangzhong Pharmaceutical Co. Ltd. as composite powder. 1 g dry composite powder was equivalent to 12.56 g total crude drugs.

1.2 Laboratory Animals

The same as in Example 51.

1.3 Primary Reagents

The same as in Example 51.

1.4 Primary Instruments

The same as in Example 51.

2. Experimental Methods
2.1 Effect of Composition 5 on Leucocyte Reduction in Mice Induced by Cyclophosphamide[1]
2.1.1 Grouping, Modeling and Dosage Regime Mice were randomly divided into 6 groups with 10 animals per group, i.e., normal control group, model control group, positive control group, and groups on low, medium and high doses of Composition 5. The low-, medium- and high-dose groups were intragastrically given Composition 5 at a dose of 2.0 g crude drug/kg, 4.0 g crude drug/kg, and 12.0 g crude drug/kg, respectively; the positive control group was intragastrically given batyl alcohol (100 mg/kg) at a dose of 0.1 ml/10 g body weight; the normal control group and the model control group were intragastrically given an equivalent volume of distilled water; and the dosage regime lasted for 15 days with one dose per day. From day 9 of intragastrical administration, all mice in each group, except the normal control group, were given cyclophosphamide at a dose of 40 mg/kg each day via subcutaneous injection for 3 consecutive days. One hour after the intragastrical administration on day 15, blood and femurs were harvested for tests.

2.1.2 Peripheral Leucocyte Assay

The same as in Example 51.

2.1.3 Bone Marrow Nucleated Cell Count (BMC)

The same as in Example 51.

2.1.4 Bone Marrow DNA Content Determination

The same as in Example 51.

2.2 Effect of Composition 5 on Leucocyte Reduction in Mice Induced by Cytarabine[2] 2.2.1 Grouping, Modeling and Dosage Regime The same as in 2.1.

2.4 Statistic Method

The same as in Example 51.

3. Results 3.1 Effect of Composition 5 on Leucocyte Reduction in Mice Induced by Cyclophosphamide Test results are shown in Tables 1 and 2. The number of peripheral WBC and the contents of bone marrow nucleated cells and DNA in the model control group decreased as compared to those in the normal control group, suggesting a successful modeling. Compared to the model control group, the number of peripheral WBC and the contents of bone marrow nucleated cells and DNA significantly increased in the Composition 5 high- and medium-dose groups and in the positive control group, and also showed a tendency to increase in the Composition 5 low-dose group, indicating that Composition 5 can resist leucocyte reduction in mice induced by cyclophosphamide and improve the hematopoietic function of the bone marrow thereof.

TABLE 1

Effect of Composition 5 on peripheral leucocyte reduction in mice induced by cyclophosphamide ($\bar{x} \pm s$, ×10$^9$)

| Groups | Dose (g crude drug/kg) | Number of animals | WBC before modeling | WBC after modeling | WBC after treatment |
|---|---|---|---|---|---|
| Normal control group | 0.0 | 10 | 9.10 ± 1.77 | 9.39 ± 2.08 | 9.55 ± 2.20 |
| Model control group | 0.0 | 10 | 9.23 ± 2.03 | 5.52 ± 1.54** | 5.88 ± 1.42** |
| Positive control group | 100 mg | 10 | 9.52 ± 2.16 | 5.73 ± 1.60** | 7.89 ± 1.60▲▲ |
| Test drug low-dose group | 2.0 | 10 | 9.44 ± 2.20 | 5.29 ± 1.53** | 7.30 ± 1.75 |
| Test drug medium-dose group | 4.0 | 10 | 9.09 ± 2.05 | 5.37 ± 1.72** | 7.64 ± 2.12▲ |
| Test drug high-dose group | 12.0 | 10 | 9.31 ± 2.17 | 5.67 ± 1.80** | 8.23 ± 1.76▲▲ |

*$P < 0.05$,
**$P < 0.01$ vs. normal control group;
▲$P < 0.05$,
▲▲$P < 0.01$ vs. model control group.

TABLE 2

Effect of Composition 5 on the contents of bone marrow BCM and DNA in mice injected with cyclophosphamide ($\bar{x} \pm s$)

| Groups | Dose (g crude drug/kg) | Number of animals | Bone marrow BCM (×10$^6$) | Bone marrow DNA |
|---|---|---|---|---|
| Normal control group | 0.0 | 10 | 16.95 ± 2.67 | 0.985 ± 0.225 |
| Model control group | 0.0 | 10 | 12.03 ± 2.40** | 0.570 ± 0.147** |
| Positive control group | 100 mg | 10 | 14.86 ± 2.28▲ | 0.755 ± 0.128▲▲ |
| Test drug low-dose group | 2.0 | 10 | 13.78 ± 2.17 | 0.681 ± 0.133 |
| Test drug medium-dose group | 4.0 | 10 | 14.56 ± 2.23▲ | 0.779 ± 0.151▲▲ |
| Test drug high-dose group | 12.0 | 10 | 15.13 ± 1.99▲▲ | 0.780 ± 0.165▲▲ |

*$P < 0.05$,
**$P < 0.01$ vs. normal control group;
▲$P < 0.05$,
▲▲$P < 0.01$ vs. model control group.

The same as in Example 51.

2.2.2 Peripheral Leucocyte Assay, Bone Marrow Nucleated Cell Count, and Bone Marrow DNA Content Determination The same as in 2.1.

2.3 Effect of Composition 5 on Leucocyte Reduction in Mice Induced by X-Ray Radiation[3]

2.3.1 Grouping, Modeling and Dosage Regime

The same as in Example 51.

2.3.2 Peripheral Leucocyte Assay, Bone Marrow Nucleated Cell Count, and Bone Marrow DNA Content Determination 3.2 Effect of Composition 5 on Leucocyte Reduction in Mice Induced by Cytarabine Test results are shown in Tables 3 and 4. The number of peripheral WBC and the contents of bone marrow nucleated cells and DNA in the model control group decreased as compared to those in the normal control group, suggesting a successful modeling. Compared to the model control group, the number of peripheral WBC and the contents of bone marrow nucleated cells and DNA significantly increased in the Composition 5 high- and medium-dose groups and in the positive control group, and also showed a tendency to increase in the Composition 5 low-dose group, indicating that Composition 5 can resist leucocyte induction in mice induced by cytarabine and improve the hematopoietic function of the bone marrow thereof.

TABLE 3

Effect of Composition 5 on peripheral leucocyte reduction in mice induced by cytarabine ($\bar{x} \pm s$, $\times 10^9$)

| Groups | Dose (g crude drug/kg) | Number of animals | WBC before modeling | WBC after modeling | WBC after treatment |
|---|---|---|---|---|---|
| Normal control group | 0.0 | 10 | 8.77 ± 1.88 | 8.90 ± 1.74 | 8.86 ± 1.69 |
| Model control group | 0.0 | 10 | 8.59 ± 1.61 | 4.77 ± 1.80** | 4.89 ± 1.38** |
| Positive control group | 100 mg | 10 | 8.44 ± 1.74 | 4.53 ± 1.28** | 7.54 ± 1.62▲▲ |
| Test drug low-dose group | 2.0 | 10 | 8.76 ± 1.83 | 4.61 ± 1.63** | 5.90 ± 1.34 |
| Test drug medium-dose group | 4.0 | 10 | 8.81 ± 1.75 | 4.82 ± 1.36** | 7.23 ± 1.45▲▲ |
| Test drug high-dose group | 12.0 | 10 | 8.65 ± 1.60 | 4.74 ± 1.53** | 7.62 ± 1.50▲▲ |

*$P < 0.05$,

**$P < 0.01$ vs. normal control group;

▲$P < 0.05$,

▲▲$P < 0.01$ vs. model control group.

TABLE 4

Effect of Composition 5 on the contents of bone marrow BCM and DNA in mice injected with cytarabine ($\bar{x} \pm s$)

| Groups | Dose (g crude drug/kg) | Number of animals | Bone marrow BCM ($\times 10^6$) | Bone marrow DNA |
|---|---|---|---|---|
| Normal control group | 0.0 | 10 | 16.24 ± 2.70 | 1.029 ± 0.218 |
| Model control group | 0.0 | 10 | 10.05 ± 2.64** | 0.654 ± 0.139** |
| Positive control group | 100 mg | 10 | 13.25 ± 2.31▲ | 0.856 ± 0.150▲▲ |
| Test drug low-dose group | 2.0 | 10 | 12.58 ± 2.28 | 0.788 ± 0.177 |
| Test drug medium-dose group | 4.0 | 10 | 13.61 ± 2.65▲ | 0.845 ± 0.158▲ |
| Test drug high-dose group | 12.0 | 10 | 14.52 ± 2.53▲▲ | 0.921 ± 0.172▲▲ |

*$P < 0.05$,

**$P < 0.01$ vs. normal control group;

▲$P < 0.05$,

▲▲$P < 0.01$ vs. model control group.

3.3 Effect of Composition 5 on Leucocyte Reduction in Mice Induced by X-Ray Radiation Test results are shown in Tables 5 and 6. The number of peripheral WBC and the contents of bone marrow nucleated cells and DNA in the model control group decreased as compared to those in the normal control group, suggesting a successful modeling. Compared to the model control group, the number of peripheral WBC and the contents of bone marrow nucleated cells and DNA significantly increased in the Composition 5 high- and medium-dose groups and in the positive control group, and also showed a tendency to increase in the Composition 5 low-dose group, indicating that Composition 5 can resist leucocyte induction in mice induced by X-ray radiation and improve the hematopoietic function of the bone marrow thereof.

TABLE 5

Effect of Composition 5 on peripheral leucocyte reduction in mice induced by X-ray radiation ($\bar{x} \pm s$, $\times 10^9$)

| Groups | Dose (g crude drug/kg) | Number of animals | WBC before modeling | WBC on day 8 after treatment | WBC on day 15 after treatment |
| --- | --- | --- | --- | --- | --- |
| Normal control group | 0.0 | 10 | 9.04 ± 2.10 | 9.24 ± 1.76 | 9.18 ± 2.02 |
| Model control group | 0.0 | 10 | 9.13 ± 2.25 | 5.56 ± 1.31** | 5.72 ± 1.66** |
| Positive control group | 100 mg | 10 | 9.09 ± 2.08 | 5.32 ± 1.54** | 7.80 ± 1.43▲▲ |
| Test drug low-dose group | 2.0 | 10 | 9.21 ± 1.90 | 5.62 ± 1.26** | 6.90 ± 1.45 |
| Test drug medium-dose group | 4.0 | 10 | 9.08 ± 2.12 | 5.61 ± 1.30** | 7.53 ± 1.28▲ |
| Test drug high-dose group | 12.0 | 10 | 9.26 ± 2.33 | 5.48 ± 1.29** | 8.10 ± 1.47▲▲ |

*$P < 0.05$,
**$P < 0.01$ vs. normal control group;
▲$P < 0.05$,
▲▲$P < 0.01$ vs. model control group.

TABLE 6

Effect of Composition 5 on the contents of bone marrow BCM and DNA in mice after X-ray radiation ($\bar{x} \pm s$)

| Groups | Dose (g crude drug/kg) | Number of animals | Bone marrow BCM ($\times 10^6$) | Bone marrow DNA |
| --- | --- | --- | --- | --- |
| Normal control group | 0.0 | 10 | 16.53 ± 2.96 | 0.105 ± 0.201 |
| Model control group | 0.0 | 10 | 11.66 ± 2.03** | 0.570 ± 0.118** |
| Positive control group | 100 mg | 10 | 13.92 ± 2.57▲ | 0.795 ± 0.127▲▲ |
| Test drug low-dose group | 2.0 | 10 | 13.50 ± 2.42 | 0.678 ± 0.145 |
| Test drug medium-dose group | 4.0 | 10 | 14.71 ± 2.60▲▲ | 0.786 ± 0.132▲▲ |
| Test drug high-dose group | 12.0 | 10 | 15.02 ± 2.33▲▲ | 0.810 ± 0.135▲▲ |

*$P < 0.05$,
**$P < 0.01$ vs. normal control group;
▲$P < 0.05$,
▲▲$P < 0.01$ vs. model control group.

4. Conclusion

The animal experiments demonstrate that Composition 5 obtained in Example 5 can resist leucocyte reduction in mice induced by cyclophosphamide, cytarabine and X-ray radiation and can improve the hematopoietic function of the bone marrow thereof, indicating that Composition 5 may be effective in preventing and treating leucopenia induced by radiotherapy and chemotherapy.

Example 56. Animal Experiment Report of Composition 6 Obtained in Example 6 in Prevention and Treatment of Leucopenia Induced by Radiotherapy or Chemotherapy 1. Materials and Methods
1.1 Sources of Samples The test drug was Composition 6 (Radix Panacis Quinquefolii, *Ganoderma*, fermented *Cordyceps sinensis* powder, *Cordyceps*, and Flos Rosae Rugosae) provided by Jiangzhong Pharmaceutical Co. Ltd. as composite powder. 1 g dry composite powder was equivalent to 13.78 g total crude drugs.

1.2 Laboratory Animals

The same as in Example 51.

1.3 Primary Reagents

The same as in Example 51.

1.4 Primary Instruments

The same as in Example 51.

2. Experimental Methods
2.1 Effect of Composition 6 on Leucocyte Reduction in Mice Induced by Cyclophosphamide[1]

2.1.1 Grouping, Modeling and Dosage Regime

Mice were randomly divided into 6 groups with 10 animals per group, i.e., normal control group, model control group, positive control group, and groups on low, medium and high doses of Composition 6. The low-, medium- and high-dose groups were intragastrically given Composition 6 at a dose of 2.0 g crude drug/kg, 4.0 g crude drug/kg, and 12.0 g crude drug/kg, respectively; the positive control group was intragastrically given batyl alcohol (100 mg/kg) at a dose of 0.1 ml/10 g body weight; the normal control group and the model control group were intragastrically given an equivalent volume of distilled water; and the dosage regime lasted for 15 days with one dose per day. From day 9 of intragastrical administration, all mice in each group, except the normal control group, were given cyclophosphamide at a dose of 40 mg/kg each day via subcutaneous injection for 3 consecutive days. One hour after the intragastrical administration on day 15, blood and femurs were harvested for tests.
2.1.2 Peripheral Leucocyte Assay
  The same as in Example 51.
2.1.3 Bone Marrow Nucleated Cell Count (BMC)
  The same as in Example 51.
2.1.4 Bone Marrow DNA Content Determination
  The same as in Example 51.
2.2 Effect of Composition 6 on Leucocyte Reduction in Mice Induced by Cytarabine[2]
2.2.1 Grouping, Modeling and Dosage Regime
  The same as in Example 51.
2.2.2 Peripheral Leucocyte Assay, Bone Marrow Nucleated Cell Count, and Bone Marrow DNA Content Determination
  The same as in 2.1.
2.3 Effect of Composition 6 on Leucocyte Reduction in Mice Induced by X-Ray Radiation[3]
2.3.1 Grouping, Modeling and Dosage Regime
  The same as in Example 51.
2.3.2 Peripheral Leucocyte Assay, Bone Marrow Nucleated Cell Count, and Bone Marrow DNA Content Determination
  The same as in 2.1.
2.4 Statistic Method
  The same as in Example 51.
3. Results
3.1 Effect of Composition 6 on Leucocyte Reduction in Mice Induced by Cyclophamide
  Test results are shown in Tables 1 and 2. The number of peripheral WBC and the contents of bone marrow nucleated cells and DNA in the model control group decreased as compared to those in the normal control group, suggesting a successful modeling. Compared to the model control group, the number of peripheral WBC and the contents of bone marrow nucleated cells and DNA significantly increased in the Composition 6 high- and medium-dose groups and in the positive control group, and also showed a tendency to increase in the Composition 6 low-dose group, indicating that Composition 6 can resist leucocyte reduction in mice induced by cyclophosphamide and improve the hematopoietic function of the bone marrow thereof.

TABLE 1

Effect of Composition 6 on peripheral leucocyte reduction in mice induced by cyclophosphamide ($\bar{x} \pm s$, $\times 10^9$)

| Groups | Dose (g crude drug/kg) | Number of animals | WBC before modeling | WBC after modeling | WBC after treatment |
|---|---|---|---|---|---|
| Normal control group | 0.0 | 10 | 10.60 ± 1.95 | 10.42 ± 2.30 | 10.54 ± 2.27 |
| Model control group | 0.0 | 10 | 10.44 ± 2.23 | 6.08 ± 1.88** | 6.31 ± 1.67** |
| Positive control group | 100 mg | 10 | 10.58 ± 2.34 | 6.25 ± 1.76** | 8.96 ± 1.93▲▲ |
| Test drug low-dose group | 2.0 | 10 | 10.72 ± 2.28 | 6.16 ± 1.93** | 7.58 ± 1.75 |
| Test drug medium-dose group | 4.0 | 10 | 10.28 ± 2.19 | 6.40 ± 1.97** | 8.22 ± 1.76▲ |
| Test drug high-dose group | 12.0 | 10 | 10.47 ± 2.23 | 6.27 ± 1.73** | 9.40 ± 1.94▲▲ |

*$P < 0.05$,
**$P < 0.01$ vs. normal control group;
▲$P < 0.05$,
▲▲$P < 0.01$ vs. model control group.

TABLE 2

Effect of Composition 6 on the contents of bone marrow BCM and DNA in mice injected with cyclophamide ($\bar{x} \pm s$)

| Groups | Dose (g crude drug/kg) | Number of animals | Bone marrow BCM ($\times 10^6$) | Bone marrow DNA |
|---|---|---|---|---|
| Normal control group | 0.0 | 10 | 17.58 ± 2.81 | 0.116 ± 0.212 |
| Model control group | 0.0 | 10 | 12.67 ± 2.52** | 0.745 ± 0.156** |
| Positive control group | 100 mg | 10 | 15.72 ± 2.34▲ | 0.958 ± 0.138▲▲ |
| Test drug low-dose group | 2.0 | 10 | 14.33 ± 2.76 | 0.842 ± 0.147 |
| Test drug medium-dose group | 4.0 | 10 | 15.28 ± 2.19▲ | 0.915 ± 0.165▲▲ |
| Test drug high-dose group | 12.0 | 10 | 16.20 ± 2.59▲▲ | 0.969 ± 0.173▲▲ |

*$P < 0.05$,
**$P < 0.01$ vs. normal control group;
▲$P < 0.05$,
▲▲$P < 0.01$ vs. model control group.

3.2 Effect of Composition 6 on Leucocyte Reduction in Mice Induced by Cytarabine Test results are shown in Tables 3 and 4. The number of peripheral WBC and the contents of bone marrow nucleated cells and DNA in the model control group decreased as compared to those in the normal control group, suggesting a successful modeling. Compared to the model control group, the number of peripheral WBC and the contents of bone marrow nucleated cells and DNA significantly increased in the Composition 6 high- and medium-dose groups and in the positive control group, and also showed a tendency to increase in the Composition 6 low-dose group, indicating that Composition 6 can resist leucocyte induction in mice induced by cytarabine and improve the hematopoietic function of the bone marrow thereof.

TABLE 3

Effect of Composition 6 on peripheral leucocyte reduction in mice induced by cytarabine ($\bar{x} \pm s$, $\times 10^9$)

| Groups | Dose (g crude drug/kg) | Number of animals | WBC before modeling | WBC after modeling | WBC after treatment |
| --- | --- | --- | --- | --- | --- |
| Normal control group | 0.0 | 10 | 10.14 ± 2.20 | 10.32 ± 2.66 | 10.44 ± 2.70 |
| Model control group | 0.0 | 10 | 10.25 ± 2.25 | 6.45 ± 1.39** | 6.15 ± 1.34** |
| Positive control group | 100 mg | 10 | 10.10 ± 2.40 | 6.62 ± 1.52** | 8.52 ± 1.55▲▲ |
| Test drug low-dose group | 2.0 | 10 | 10.33 ± 2.18 | 6.77 ± 1.70** | 7.48 ± 1.70 |
| Test drug medium-dose group | 4.0 | 10 | 10.51 ± 2.23 | 6.38 ± 1.54** | 8.45 ± 1.66▲▲ |
| Test drug high-dose group | 12.0 | 10 | 10.44 ± 2.16 | 6.50 ± 1.61** | 8.62 ± 1.47▲▲ |

*$P < 0.05$,

**$P < 0.01$ vs. normal control group;

▲$P < 0.05$,

▲▲$P < 0.01$ vs. model control group.

TABLE 4

Effect of Composition 6 on the contents of bone marrow BCM and DNA in mice injected with cytarabine ($\bar{x} \pm s$)

| Groups | Dose (g crude drug/kg) | Number of animals | Bone marrow BCM ($\times 10^6$) | Bone marrow DNA |
| --- | --- | --- | --- | --- |
| Normal control group | 0.0 | 10 | 15.89 ± 2.70 | 0.973 ± 0.209 |
| Model control group | 0.0 | 10 | 9.66 ± 2.05** | 0.625 ± 0.143** |
| Positive control group | 100 mg | 10 | 13.58 ± 2.17▲ | 0.830 ± 0.116▲ |
| Test drug low-dose group | 2.0 | 10 | 11.87 ± 2.64 | 0.756 ± 0.170 |
| Test drug medium-dose group | 4.0 | 10 | 12.30 ± 2.38▲ | 0.818 ± 0.180▲ |
| Test drug high-dose group | 12.0 | 10 | 14.19 ± 2.49▲▲ | 0.900 ± 0.166▲▲ |

*$P < 0.05$,

**$P < 0.01$ vs. normal control group;

▲$P < 0.05$,

▲▲$P < 0.01$ vs. model control group.

3.3 Effect of Composition 6 on Leucocyte Reduction in Mice Induced by X-Ray Radiation Test results are shown in Tables 5 and 6. The number of peripheral WBC and the contents of bone marrow nucleated cells and DNA in the model control group decreased as compared to those in the normal control group, suggesting a successful modeling. Compared to the model control group, the number of peripheral WBC and the contents of bone marrow nucleated cells and DNA significantly increased in the Composition 6 high- and medium-dose groups and in the positive control group, and also showed a tendency to increase in the Composition 6 low-dose group, indicating that Composition 6 can resist leucocyte induction in mice induced by X-ray radiation and improve the hematopoietic function of the bone marrow thereof.

TABLE 5

Effect of Composition 6 on peripheral leucocyte reduction in mice induced by X-ray radiation ($\bar{x} \pm s$, $\times 10^9$)

| Groups | Dose (g crude drug/kg) | Number of animals | WBC before modeling | WBC on day 8 after treatment | WBC on day 15 after treatment |
| --- | --- | --- | --- | --- | --- |
| Normal control group | 0.0 | 10 | 9.88 ± 2.16 | 9.66 ± 1.76 | 9.78 ± 2.43 |
| Model control group | 0.0 | 10 | 9.72 ± 2.09 | 5.90 ± 1.55** | 5.70 ± 1.82** |
| Positive control group | 100 mg | 10 | 9.65 ± 2.22 | 5.53 ± 1.28** | 8.03 ± 1.59▲▲ |
| Test drug low-dose group | 2.0 | 10 | 9.84 ± 1.70 | 5.76 ± 1.44** | 7.24 ± 1.60 |
| Test drug medium-dose group | 4.0 | 10 | 9.73 ± 2.26 | 5.81 ± 1.39** | 7.90 ± 1.44▲▲ |
| Test drug high-dose group | 12.0 | 10 | 9.55 ± 2.01 | 5.72 ± 1.70** | 8.34 ± 1.75▲▲ |

*$P < 0.05$,
**$P < 0.01$ vs. normal control group;
▲$P < 0.05$,
▲▲$P < 0.01$ vs. model control group.

TABLE 6

Effect of Composition 6 on the contents of bone marrow BCM and DNA in mice after X-ray radiation ($\bar{x} \pm s$)

| Groups | Dose (g crude drug/kg) | Number of animals | Bone marrow BCM ($\times 10^6$) | Bone marrow DNA |
| --- | --- | --- | --- | --- |
| Normal control group | 0.0 | 10 | 16.26 ± 2.78 | 0.996 ± 0.222 |
| Model control group | 0.0 | 10 | 11.41 ± 2.62** | 0.563 ± 0.121** |
| Positive control group | 100 mg | 10 | 14.78 ± 2.44▲▲ | 0.780 ± 0.135▲▲ |
| Test drug low-dose group | 2.0 | 10 | 13.02 ± 2.55 | 0.665 ± 0.160 |
| Test drug medium-dose group | 4.0 | 10 | 14.35 ± 2.32▲▲ | 0.772 ± 0.144▲▲ |
| Test drug high-dose group | 12.0 | 10 | 14.66 ± 2.09▲▲ | 0.801 ± 0.127▲▲ |

*$P < 0.05$,
**$P < 0.01$ vs. normal control group;
▲$P < 0.05$,
▲▲$P < 0.01$ vs. model control group.

4. Conclusion

The animal experiments demonstrate that Composition 6 obtained in Example 6 can resist leucocyte reduction in mice induced by cyclophosphamide, cytarabine and X-ray radiation and can improve the hematopoietic function of the bone marrow thereof, indicating that Composition 6 may be effective in preventing and treating leucopenia induced by radiotherapy and chemotherapy.

The invention claimed is:

1. A method of treating or reducing the incidence of leucopenia induced by radiotherapy or chemotherapy, comprising the step of administering to a subject in need thereof a composition made from raw materials comprising as sole active ingredients:

(i) *Ganoderma*, Radix Panacis Quinquefolii or Radix Et Rhizoma Ginseng, fermented *Cordyceps sinensis* powder and/or *Cordyceps*, and (ii) one or more of Flos Rosae Rugosae in an amount of 5 to 90 parts, *Ganoderma* spore powder in an amount of 5 to 150 parts, *Ganoderma* spore oil in an amount of 1 to 90 parts, Radix Pseudostellariae in an amount of 10 to 400 parts, Folium Ginseng in an amount of 1 to 120 parts, Radix *Codonopsis* in an amount of 3 to 400 parts, and Radix Astragali in an amount of 3 to 400 parts, or any combination thereof.

2. The method of claim 1, characterized in that the raw materials comprise one or more of 10 to 60 parts of Flos Rosae Rugosae, 10 to 120 parts of *Ganoderma* spore powder, 10 to 60 parts of *Ganoderma* spore oil, 20 to 200 parts of Radix Pseudostellariae, 20 to 90 parts of Folium Ginseng, 20 to 200 parts of Radix *Codonopsis*, and 20 to 200 parts of Radix Astragali, or any combination thereof.

3. The method of claim 2, characterized in that the raw materials comprise one or more of 30 parts of Flos Rosae Rugosae, 30 parts of *Ganoderma* spore powder, 20 parts of *Ganoderma* spore oil, 40 parts of Radix Pseudostellariae, 30 parts of Folium Ginseng, 40 parts of Radix *Codonopsis*, and 40 parts of Radix Astragali, or any combination thereof.

4. The method of claim 1, characterized in that the raw materials comprise 5 to 200 parts of *Ganoderma*, 5 to 150 parts of Radix Panacis Quinquefolii or Radix Et Rhizoma Ginseng, 1 to 90 parts of fermented *Cordyceps sinensis* powder and/or 1 to 120 parts of *Cordyceps*, and 5 to 90 parts of Flos Rosae Rugosae.

5. The method of claim 4, characterized in that the raw materials comprise 20 to 120 parts of *Ganoderma*, 10 to 90 parts of Radix Panacis Quinquefolii or Radix Et Rhizoma Ginseng, 3 to 60 parts of fermented *Cordyceps sinensis* powder and/or 3 to 90 parts of *Cordyceps*, and 10 to 60 parts of Flos Rosae Rugosae.

6. The method of claim 5, characterized in that the raw materials comprise 40 parts of *Ganoderma*, 30 parts of Radix Panacis Quinquefolii or Radix Et Rhizoma Ginseng, 20 parts of fermented *Cordyceps sinensis* powder and/or 6.7 parts of *Cordyceps*, and 30 parts of Flos Rosae Rugosae.

7. The method of claim 1, characterized in that the raw materials comprise:
   5 to 200 parts of *Ganoderma*, 5 to 150 parts of Radix Panacis Quinquefolii or Radix Et Rhizoma Ginseng, 1 to 90 parts of fermented *Cordyceps sinensis* powder and/or 1 to 120 parts of *Cordyceps*, and 5 to 90 parts of Flos Rosae Rugosae, and
   one or more of 5 to 150 parts of *Ganoderma* spore powder, 1 to 90 parts of *Ganoderma* spore oil, 10 to 400 parts of Radix Pseudostellariae, 1 to 120 parts of Folium Ginseng, 3 to 400 parts of Radix *Codonopsis*, and 3 to 400 parts of Radix Astragali, or any combination thereof.

8. The method of claim 1, characterized in that the species to which the fermented *Cordyceps sinensis* powder belongs is one of or any combination of: *Paecilomyces hepialli* Chen et Dai, sp.nov, Mortiscrslla hepialid C.T.&B.liu, *Synnematium sinensis* Yin & Shen, *Gliocladium roseum* (link)Thom, *Mortierella* sp., *Cephalosporium sinensis* Chen sp.nov, or *Hirsutella sinensis* Liu, Guo, Yu-et Zeng, sp.nov.

9. The method of claim 1, wherein the *Ganoderma* spore powder is sporoderm-broken *Ganoderma* spore powder.

10. The method of claim 1, further comprising the step of adding thereto auxiliary agent(s) or excipient(s) which is/are acceptable in health care products and/or in medicaments.

11. The method of claim 10, characterized in that the dosage form of the composition is any one of a tablet, an oral liquid, a granule, a capsule, an electuary, a dripping pill, a pill, powder, a lozenge, a fluid extract, an extract, an injection, and a syrup.

12. The method of claim 1, characterized in that the composition made from the raw materials is prepared by mixing the raw materials; or by mixing the raw materials and extracting them with water and/or alcohol to obtain the composition; or by extracting one or more of the raw materials with water and/or alcohol and using the extract as the active ingredient to prepare the composition.

13. The method of claim 12, characterized in that the composition made from the raw materials is prepared by the following steps:
   1) weighing out traditional Chinese drugs as the raw materials; and
   2) extracting the raw materials under reflux with alcohol or water, so as to obtain a liquid extract as the active ingredient, and adding auxiliary agent(s) to prepare various dosage forms.

14. The method of claim 12, characterized in that the composition made from the raw materials is prepared by the following steps:
   1) weighing out traditional Chinese drugs as the raw materials, adding methanol or ethanol thereto to carry out extraction, recovering methanol or ethanol from the extraction liquid, to obtain Extract I;
   2) evaporating methanol or ethanol from the residual drugs, adding water to carry out extraction, to obtain Extract II; and
   3) combining Extract I and Extract II, carrying out filtration, concentrating the filtrate to an appropriate amount, adding pharmaceutically conventional auxiliary agent(s) to prepare a desired formulation by a pharmaceutically conventional process.

15. The method of claim 12, characterized in that the composition made from the raw materials is prepared by the following steps:
   1) raw material preparation: weighing out traditional Chinese drugs as the raw materials;
   2) extraction and concentration: soaking the Chinese drug raw materials processed in step 1) in water, then decocting several times by heating, combining the liquid extracts to carry out filtration, concentrating the filtrate to an appropriate amount, cooling the concentrate and subjecting it to high-speed centrifugation to remove impurities, and reserving the product until use; and
   3) formulation preparation: preparing the concentrate obtained in step 2), alone or together with medicinally acceptable auxiliary agent(s), into a desired formulation by a pharmaceutically conventional process.

16. The method of claim 15, characterized in that, in step 2), the soaking time is 20 to 60 min, and after soaking, decocting is carried out 1 to 3 times by heating, with each decoction lasting for 1 to 2 h and having a 6 to 13-fold amount of water added.

17. The method of claim 12, characterized in that the alcohol is methanol or ethanol.

18. The method of claim 14, characterized in that the concentration of the methanol is 5% to 95%, and the concentration of the ethanol is 5% to 95%.

* * * * *